United States Patent
Janssen et al.

(10) Patent No.: US 7,105,522 B2
(45) Date of Patent: Sep. 12, 2006

(54) HIV INHIBITING PYRAZINONE DERIVATIVES

(75) Inventors: Paul Adriaan Jan Janssen, Beerse (BE); Koen Jeanne Alfons Van Aken, Kortrijk (BE); Paulus Joannes Lewi, Turnhout (BE); Lucien Maria Henricus Koymans, Retie (BE); Marc René de Jonge, Tilburg (NL); Jan Heeres, Vosselaar (BE); Frederik Frans Desire Daeyaert, Beerse (BE); Georges Joseph Cornelius Hoornaert, Kessel-Lo (BE); Frans Josef Cornelius Compernolle, Herent (BE); Amuri Kilonda, Kessel-Lo (BE)

(73) Assignee: Janssen Pharmaceutica, N.V., Beerse (BE)

( * ) Notice: Subject to any disclaimer, the term of this patent is extended or adjusted under 35 U.S.C. 154(b) by 281 days.

(21) Appl. No.: 10/468,447

(22) PCT Filed: Mar. 13, 2002

(86) PCT No.: PCT/EP02/02806

§ 371 (c)(1), (2), (4) Date: Aug. 20, 2003

(87) PCT Pub. No.: WO02/078708

PCT Pub. Date: Oct. 10, 2002

(65) Prior Publication Data

US 2004/0102456 A1   May 27, 2004

(30) Foreign Application Priority Data

Mar. 15, 2001   (EP) .................................. 01200971

(51) Int. Cl.
- *A61K 31/4965* (2006.01)
- *C07D 401/00* (2006.01)
- *C07D 403/00* (2006.01)
- *C07D 405/00* (2006.01)
- *C07D 241/02* (2006.01)

(52) U.S. Cl. ................. 514/255.06; 544/405; 544/406; 544/407; 544/408; 544/409

(58) Field of Classification Search ........... 514/255.06; 544/405, 406, 407, 408, 409

See application file for complete search history.

(56) References Cited

FOREIGN PATENT DOCUMENTS

| | | |
|---|---|---|
| EP | 0462800 | 12/1991 |
| GB | 2266716 | 11/1993 |
| WO | WO 98/11075 | * 3/1998 |

* cited by examiner

Primary Examiner—James O. Wilson
Assistant Examiner—Zachary C. Tucker

(57) ABSTRACT

This invention concerns a compound of formula

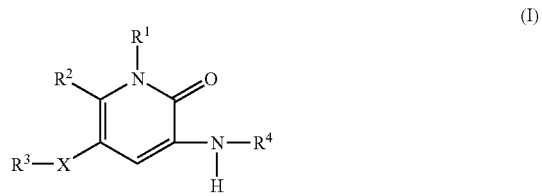

(I)

a N-oxide, a pharmaceutically acceptable addition salt, a quaternary amine and a stereochemically isomeric form thereof, wherein $R^1$ is hydrogen, hydroxy, cyano, amino, mono-or di($C_{1-4}$alkyl)amino, formyl, carboxyl, $C_{1-6}$alkyl, hydroxy$C_{1-6}$alkyl, polyhalo$C_{1-6}$alkyl, $C_{2-6}$alkenyl, $C_{2-6}$alkynyl, $C_{3-7}$cycloalkyl, $C_{1-6}$alkyloxy, $C_{1-6}$alkylcarbonyl, aminocarbonyl, —S(=O)$_m$—NH$_2$, mono-or di($C_{1-4}$alkyl)aminocarbonyl, $C_{1-6}$alkyloxycarbonyl, $C_{1-6}$alkylcarbonyloxy, aryl, aryl$C_{1-6}$alkyl or aryloxy; $R^2$ is hydrogen; halo; mercapto; formyl; cyano; carboxy; azido; hydroxy; oxiranyl; amino; mono- or di($C_{1-4}$alkyl)amino; formylamino; $R^5R^6N$—C(=O)—; $R^7$—N=C($R^8$)—; $C_{1-6}$alkyl-S(=O)m; aryl-S(=O)$_m$; optionally substituted $C_{2-6}$alkenyl; optionally substituted $C_{2-6}$alkynyl; $C_{1-6}$alkyloxy; hydroxy$C_{1-6}$alkyloxy; amino$C_{1-6}$alkyloxy; mono- or di($C_{1-4}$alkyl)amino-$C_{1-6}$alkyloxy; $C_{1-6}$alkylcarbonyl; arylcarbonyl; Het$^1$carbonyl; $C_{1-6}$alkyloxycarbonyl; $C_{1-6}$alkylcarbonyloxy; aryl; aryloxy; aryl$C_{1-6}$alkyloxy; arylthio; aryl$C_{1-6}$alkylthio; mono- or di(aryl)amino; Het$^1$; Het$^1$oxy; Het$^1$thio; Het$^1$C$_{1-6}$alkyloxy; Het$^1$C$_{1-6}$alkylthio; mono- or di(Het$^1$)amino; $C_{3-7}$cycloalkyl; $C_{3-7}$cycloalkyloxy; $C_{3-7}$cycloalkylthio; $C_{1-6}$alkylthio; hydroxy$C_{1-6}$alkylthio; amino$C_{1-6}$alkylthio; mono- or di($C_{1-4}$alkyl)amino$C_{1-6}$alkylthio; optionally substituted $C_{1-6}$alkyl; $R^3$ or $R^4$ each independently represent optionally be substituted phenyl, pyridyl, pyrimidinyl, pyrazinyl or pyridazinyl; —X— is a bivalent radical selected from —NR$^{14}$—, —NH—NH—, —N=N—, —O—, —$C_{1-6}$alkanediyl-, —C(=O)—, —CHOH—, —S—, —S(=O)$_m$—; aryl is optionally substituted phenyl; Het$^1$, Het$^2$ or Het$^3$ represent an optionally substituted monocyclic or bicyclic heterocycle; their use as a medicine, their processes for preparation and pharmaceutical compositions comprising them.

23 Claims, No Drawings

HIV INHIBITING PYRAZINONE DERIVATIVES

CROSS REFERENCE TO RELATED APPLICATIONS

This Application is a 35 U.S.C. 0 371 national phase application of PCT/EP02/02806, with an international filing date of Mar. 13, 2002, which claims priority to application EP 01200971.8, filed on Mar. 15, 2001, all of which are incorporated herein by reference in their entirety.

The present invention concerns pyrazinone derivatives having Human Immunodeficiency Virus (HIV) replication inhibiting properties. It also relates to their use as a medicine, their processes for preparation and pharmaceutical compositions comprising them.

GB 2,266,716 discloses pyrazine derivatives having HIV reverse transcriptase inhibiting activity.

WO 98/11075 describes pyrazinone derivatives as CRF (Corticotropin Releasing Factor) antagonists.

The present compounds differ from the prior art compounds by their structure or their activity, in particular their improved HIV replication inhibiting properties.

The present invention relates to novel compounds having the formula

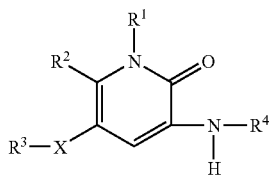

(I)

the N-oxides, pharmaceutically acceptable addition salts, quaternary amines and stereochemically isomeric forms thereof, wherein $R^1$ is hydrogen, hydroxy, cyano, amino, mono- or di($C_{1-4}$alkyl)amino, formyl, carboxyl, $C_{1-6}$alkyl, hydroxy$C_{1-6}$alkyl, polyhalo$C_{1-6}$alkyl, $C_{2-6}$alkenyl, $C_{2-6}$alkynyl, $C_{3-7}$cycloalkyl, $C_{1-6}$alkyloxy, $C_{1-6}$alkylcarbonyl, aminocarbonyl, —S(=O)$_m$—NH$_2$, mono- or di($C_{1-4}$alkyl)aminocarbonyl, $C_{1-6}$alkyloxycarbonyl, $C_{1-6}$alkylcarbonyloxy, aryl, aryl$C_{1-6}$alkyl or aryloxy;

$R^2$ is hydrogen; halo; mercapto; formyl; cyano; carboxyl; azido; hydroxy; oxiranyl; amino; mono- or di($C_{1-4}$alkyl)amino; formylamino; $R^5R^6N$—C(=O)—; $R^7$—N=C($R^8$)—; $C_{1-6}$alkyl-S(=O)$_m$; aryl-S(=O)$_m$; $C_{2-6}$alkenyl optionally substituted with one or two substituents each independently selected from halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, N-hydroxy-imino, aryl or Het$^1$; $C_{2-6}$alkynyl optionally substituted with one or two substituents each independently selected from halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, N-hydroxyimino, aryl or Het$^1$; $C_{1-6}$alkyloxy; hydroxy$C_{1-6}$alkyloxy; amino$C_{1-6}$alkyloxy; mono- or di($C_{1-4}$alkyl)amino-$C_{1-6}$alkyloxy; $C_{1-6}$alkylcarbonyl; arylcarbonyl; Het$^1$carbonyl; $C_{1-6}$alkyloxycarbonyl; $C_{1-6}$alkylcarbonyloxy; aryl; aryloxy; aryl$C_{1-6}$alkyloxy; arylthio; aryl$C_{1-6}$alkylthio; mono- or di(aryl)amino; Het$^1$; Het$^1$oxy; Het$^1$thio; Het$^1C_{1-6}$alkyloxy; Het$^1C_{1-6}$alkylthio; mono- or di(Het$^1$)amino; $C_{3-7}$cycloalkyl; $C_{3-7}$cycloalkyloxy; $C_{3-7}$cycloalkylthio; $C_{1-6}$alkylthio; hydroxy$C_{1-6}$alkylthio; amino$C_{1-6}$alkylthio; mono- or di($C_{1-4}$alkyl)amino$C_{1-6}$alkylthio; $C_{1-6}$alkyl optionally substituted with one, two or three substituents each independently selected from halo, hydroxy, cyano, $C_{1-6}$alkyloxy, $C_{1-6}$alkylthio, hydroxy-$C_{1-6}$alkyloxy, $C_{1-6}$alkyloxy, $C_{1-6}$alkyloxy$C_{1-6}$alkyloxy, $C_{1-6}$alkylcarbonyl, $C_{1-6}$alkylcarbonyloxy, aminocarbonyloxy, mono- or di($C_{1-4}$alkyl)aminocarbonyloxy, $C_{1-6}$alkyloxycarbonyl, $C_{1-6}$alkyloxycarbonyl-$C_{1-6}$alkyloxy, $C_{1-6}$alkyloxycarbonyl$C_{1-6}$alkylthio, aryl, Het$^1$, aryloxy, arylthio, aryl$C_{1-6}$alkyloxy, aryl$C_{1-6}$alkylthio, Het$^1C_{1-6}$alkyloxy, Het$^1C_{1-6}$alkylthio, $C_{1-6}$alkyl-S(=O)$_m$-oxy, amino, mono- or di($C_{1-6}$alkyl)amino, formylamino, $C_{1-6}$alkyloxycarbonylamino, $C_{1-6}$alkyloxy$C_{1-6}$alkylcarbonylamino; mono- or di(aryl)amino, mono- or di(aryl$C_{1-4}$alkyl)amino, ($C_{1-6}$alkyl)(aryl$C_{1-4}$alkyl)amino, mono- or di($C_{1-4}$alkyloxy$C_{1-4}$alkyl)amino, mono- or di(aryl$C_{1-4}$ alkyloxy-$C_{1-4}$alkyl)amino, mono- or di($C_{1-4}$alkylthio$C_{1-4}$ alkyl)amino, mono- or di(aryl$C_{1-4}$alkylthio$C_{1-4}$alkyl)amino, mono- or di(Het$^1C_{1-4}$alkyl)amino, mono- or di($C_{1-4}$ alkyl)amino$C_{1-4}$alkyloxy, mono- or di($C_{1-4}$alkyl)amino$C_{1-4}$alkylthio, $R^9$—C(=O)—NH—, $R^{10}$—NH—C(=O)—NH—, $R^{11}$—S(=O)$_2$—NH—, or a radical of formula

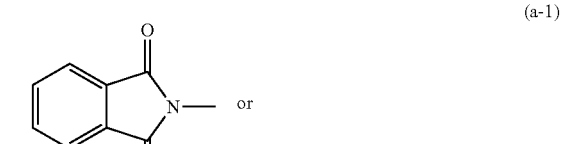

(a-1)

(a-2)

(a-3)

with $A_1$ representing CH or N, and $A_2$ representing $CH_2$, $NR^{12}$ or O, provided that when $A_1$ is CH then $A_2$ is other than $CH_2$, said radical of formula (a-1), (a-2) or (a-3) optionally being substituted with one or two substituents each independently selected from hydrogen, $C_{1-6}$alkyl, $C_{1-6}$alkyloxy, hydroxy$C_{1-4}$alkyl, $C_{1-6}$alkyloxycarbonyl, $C_{1-6}$alkyloxycarbonyl-$C_{1-4}$alkyl, amino$C_{1-6}$alkyl, carbonyl, hydroxy, cyano, amide, mono- or di($C_{1-4}$alkyl)aminocarbonyl, mono- or di($C_{1-4}$alkyl)amino$C_{1-6}$alkyl, 4-hydroxy-phenyl, 4-cyano-phenyl;

$R^3$ and $R^4$ each independently represent phenyl, pyridyl, pyrimidinyl, pyrazinyl or pyridazinyl, wherein each of said aromatic rings may optionally be substituted with one, two, three, four or five substituents each independently selected from hydroxy, halo, $C_{1-6}$alkyl optionally substituted with cyano or —C(=O)$R^{13}$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, aminocarbonyl, nitro, amino, mono- or di($C_{1-6}$alkyl)amino, polyhalo$C_{1-6}$alkyl, polyhalo$C_{1-6}$alkyloxy, polyhalo$C_{1-6}$alkylthio, —S(=O)$_pR^{13}$, —NH—S(=O)$_pR^{13}$, —C(=O)$R^{13}$, —NHC(=O)H, —C(=O)NHNH$_2$, —NHC(=O)R$^{13}$, —C(=NH)R$^{13}$ or a radical of formula

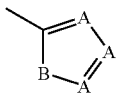
(b)

wherein each A independently is N, CH or CR$^{13}$;
B is NH, O, S or NR$^{13}$;
p is 1 or 2; and
—X— is a bivalent radical selected from —NR$^{14}$—; —NH—NH—; —N=N—; —O—; —C$_{1-6}$alkanediyl- which may optionally be substituted with halo, C$_{1-6}$alkyloxy, C$_{1-6}$alkyloxycarbonyl, C$_{1-6}$alkylcarbonyloxy, mono- or di(C$_{1-6}$alkyl)amino, mono- or di(C$_{1-6}$alkyl)aminocarbonyl; —C(=O)—; —CHOH—; —S—; —S(=O)$_m$-;
each m independently is 1 or 2;
R$^5$ and R$^6$ each independently represent hydrogen or C$_{1-4}$alkyl optionally substituted with cyano, C$_{1-4}$alkyloxy, C$_{1-4}$alkylthio, amino, mono- or di(C$_{1-4}$alkyl)amino or a radical of formula

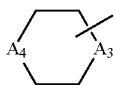
(c)

with A$_3$ and A$_4$ each independently representing CH$_2$, NR$^{12}$ or O;
R$^7$ is hydrogen, hydroxy, C$_{1-4}$alkyloxy, carboxyC$_{1-4}$alkyloxy, C$_{1-4}$alkyloxycarbonylC$_{1-4}$alkyloxy, C$_{2-4}$alkenyloxy, C$_{2-4}$alkynyloxy or arylC$_{1-4}$alkyloxy;
R$^8$ is hydrogen, carboxyl or C$_{1-4}$alkyl;
R$^9$ is hydrogen; C$_{1-4}$alkyl optionally substituted with cyano, C$_{1-4}$alkyloxy, C$_{1-4}$alkyl-S(=O)$_m$—, aryl or Het$^2$; C$_{1-4}$alkyloxy; C$_{2-4}$alkenyl; arylC$_{2-4}$alkenyl; Het$^2$C$_{2-4}$alkenyl; C$_{2-4}$alkynyl; Het$^2$C$_{2-4}$alkynyl; arylC$_{2-4}$alkynyl; C$_{3-7}$cycloalkyl; aryl; naphthyl; or Het$^2$;
R$^{10}$ is C$_{1-4}$alkyl, arylC$_{1-4}$alkyl, aryl, arylcarbonyl, C$_{1-4}$alkylcarbonyl, C$_{1-4}$alkyloxycarbonyl, C$_{1-4}$alkyloxycarbonylC$_{1-4}$alkyl;
R$^{11}$ is C$_{1-4}$alkyl optionally substituted with aryl or Het$^3$, polyhaloC$_{1-4}$alkyl, or C$_{2-4}$alkenyl optionally substituted with aryl or Het$^3$;
R$^{12}$ is hydrogen, C$_{1-4}$alkyl or C$_{1-4}$alkylcarbonyl;
R$^{13}$ is C$_{1-6}$alkyl, amino, mono- or di(C$_{1-6}$alkyl)amino or polyhaloC$_{1-6}$alkyl;
R$^{14}$ is hydrogen; aryl; formyl; C$_{1-6}$alkylcarbonyl; C$_{1-6}$alkyl; C$_{1-6}$alkyloxycarbonyl; C$_{1-6}$alkyl substituted with formyl, C$_{1-6}$alkylcarbonyl, C$_{1-6}$alkyloxycarbonyl, C$_{1-6}$alkylcarbonyloxy; C$_{1-6}$alkyloxyC$_{1-4}$alkylcarbonyl substituted with C$_{1-6}$alkyloxycarbonyl;
aryl is phenyl optionally substituted with one, two, three, four or five substituents each independently selected from hydroxy, halo, C$_{1-6}$alkyl, C$_{3-7}$cycloalkyl, C$_{1-6}$alkyloxy, cyano, nitro, polyhaloC$_{1-6}$alkyl and polyhaloC$_{1-6}$alkyloxy;
Het$^1$ represents a monocyclic or bicyclic heterocycle selected from pyrrolyl, furanyl, thienyl, imidazolyl, oxazolyl, thiazolyl, pyridyl, pyrimidinyl, pyrazinyl, pyridazinyl, pyrrolidinyl, tetrahydrofuranyl, tetrahydrothienyl, imidazolidinyl, oxazolidinyl, thiazolidinyl, piperidinyl, hexahydropyrimidinyl, piperazinyl, hexahydropyridazinyl, benzopyrrolyl, benzofuranyl, benzothienyl, benzimidazolyl, benzoxazolyl, benzothiazolyl, quinolinyl, 2-oxo-1,2-dihydroquinolinyl, each of said monocyclic or bicyclic heterocycle may optionally be substituted with one, two or three substituents each independently selected from halo, hydroxy, C$_{1-4}$alkyl, C$_{1-4}$alkyloxy, C$_{1-4}$alkylcarbonyl or polyhaloC$_{1-4}$alkyl;
Het$^2$ represents a monocyclic or bicyclic heterocycle selected from pyrrolyl, furanyl, thienyl, imidazolyl, oxazolyl, thiazolyl, pyrazolyl, isoxazolyl, isothiazolyl, pyridinyl, pyrimidinyl, pyrazinyl, pyridazinyl, benzopyrrolyl, benzofuranyl, benzothienyl, benzimidazolyl, benzoxazolyl, benzothiazolyl, benzotriazolyl, quinolinyl, 2-oxo-1,2-dihydro-quinolinyl, quinolinonyl, pyrrolidinyl, tetrahydrofuranyl, tetrahydrothienyl, imidazolidinyl, oxazolidinyl, thiazolidinyl, piperidinyl, hexahydropyrimidinyl, piperazinyl, hexahydropyridazinyl or a radical of formula

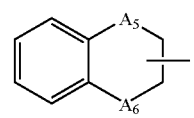
(d)

with A$_5$ or A$_6$ each independently being selected from CH$_2$ or O; each of said monocyclic or bicyclic heterocycle may optionally be substituted with one, two or three substituents each independently selected from halo, hydroxy, C$_{1-4}$alkyl, C$_{1-4}$alkyloxy, C$_{1-4}$alkylcarbonyl, polyhaloC$_{1-4}$alkyl or aryl;
Het$^3$ represents a monocyclic heterocycle selected from pyrrolyl, furanyl, thienyl, imidazolyl, oxazolyl, thiazolyl, pyridyl, pyrimidinyl, pyrazinyl, pyridazinyl, each of said heterocycle may optionally be substituted with one, two or three substituents each independently selected from halo, hydroxy, C$_{1-4}$alkyl, C$_{1-4}$alkyloxy, C$_{1-4}$alkylcarbonyl or polyhaloC$_{1-4}$alkyl.

As used hereinbefore or hereinafter C$_{1-2}$alkyl as a group or part of a group defines methyl or ethyl; C$_{1-3}$alkyl as a group or part of a group defines straight or branched chain saturated hydrocarbon radicals having from 1 to 3 carbon atoms such as methyl, ethyl, propyl, 1-methylethyl; C$_{1-4}$alkyl as a group or part of a group defines straight or branched chain saturated hydrocarbon radicals having from 1 to 4 carbon atoms such as the group defined for C$_{1-3}$alkyl and butyl, 1-methyl-propyl and the like; C$_{1-6}$alkyl as a group or part of a group defines straight or branched chain saturated hydrocarbon radicals having from 1 to 6 carbon atoms such as the group defined for C$_{1-4}$alkyl and pentyl, hexyl, 2-methylbutyl and the like; C$_{1-6}$alkanediyl defines straight or branched chain saturated bivalent hydrocarbon radicals having from 1 to 6 carbon atoms such as methylene, 1,2-ethanediyl or 1,2-ethylidene, 1,3-propanediyl or 1,3-propylidene, 1,4-butanediyl or 1,4-butylidene, 1,5-pentylidene, 1,6-hexylidene and the like; C$_{2-4}$alkenyl defines straight and branched chain hydrocarbon radicals having from 2 to 4 carbon atoms containing a double bond such as ethenyl, propenyl, butenyl and the like; C$_{2-6}$alkenyl defines straight and branched chain hydrocarbon radicals having from 2 to 6 carbon atoms containing a double bond such as the group defined for C$_{2-4}$alkenyl and pentenyl, hexenyl and the like; C$_{2-4}$alkynyl defines straight and branched chain hydrocarbon radicals having from 2 to 4 carbon atoms containing a triple bond such as ethynyl, propynyl, butynyl and the like; $C_{2-6}$alkynyl defines straight and branched chain hydrocarbon radicals having from 2 to 6 carbon atoms containing a triple bond such as the group defined for $C_{2-4}$alkynyl and pentynyl, hexynyl and the like; $C_{3-7}$cycloalkyl is generic to cyclopropyl, cyclobutyl, cyclopentyl, cyclohexyl and cycloheptyl.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalomethyl as a group or part of a group is defined as mono- or polyhalosubstituted methyl, in particular methyl with one or more fluoro atoms, for example, difluoromethyl or trifluoromethyl; polyhalo$C_{1-6}$alkyl as a group or part of a group is defined as mono- or polyhalosubstituted $C_{1-6}$alkyl, for example, the groups defined in halomethyl, 1,1-difluoroethyl and the like. In case more than one halogen atoms are attached to an alkyl group within the definition of polyhalomethyl or polyhalo$C_{1-6}$alkyl, they may be the same or different.

$Het^1$, $Het^2$ and $Het^3$ are meant to include all the possible isomeric forms of the heterocycles mentioned in the definition of $Het^1$, $Het^2$ and $Het^3$. For instance, when $Het^1$, $Het^2$ or $Het^3$ represent pyrrolyl, this also includes 2H-pyrrolyl The $Het^1$, $Het^2$ or $Het^3$ radical may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like.

When any variable (eg. aryl, $R^{13}$ etc.) occurs more than one time in any constituent, each definition is independent.

Lines drawn into ring systems indicate that the bond may be attached to any of the suitable ring atoms.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. In particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The N-oxide forms of the present compounds are meant to comprise the compounds of formula (I) wherein one or several tertiary nitrogen atoms are oxidized to the so-called N-oxide.

Some of the compounds of formula (I) may also exist in their tautomeric form. Such forms although not explicitly indicated in the above formula are intended to be included within the scope of the present invention.

Whenever used hereinafter, the term "compounds of formula (I)" is meant to also include their N-oxide forms, their salts, their quaternary amines and their stereochemically isomeric forms. Of special interest are those compounds of formula (I) which are stereochemically pure.

An interesting group of compounds of formula (I) are those compounds wherein $R^1$ is hydrogen, $C_{1-6}$alkyl, hydroxy$C_{1-6}$alkyl, polyhalo$C_{1-6}$alkyl, $C_{2-6}$alkenyl, $C_{2-6}$alkynyl, aryl, aryl$C_{1-6}$alkyl or aryloxy;

$R^2$ is hydrogen; halo; $C_{1-6}$alkyloxy; hydroxy$C_{1-6}$alkyloxy; amino$C_{1-6}$alkyloxy; mono- or di($C_{1-4}$alkyl)amino-$C_{1-6}$alkyloxy; aryl; aryloxy; aryl$C_{1-6}$alkyloxy; arylthio; aryl$C_{1-6}$alkylthio; Het$^1$; Het$^1$oxy; Het$^1$thio; Het$^1C_{1-6}$alkyloxy; Het$^1C_{1-6}$alkylthio; $C_{1-6}$alkyl optionally substituted with one, two or three substituents each independently selected from halo, hydroxy, cyano, $C_{1-6}$alkyloxy, $C_{1-6}$alkylthio, aryl, Het$^1$, aryloxy, arylthio, aryl$C_{1-6}$alkyloxy, aryl$C_{1-6}$alkylthio, Het$^1C_{1-6}$alkyloxy, Het$^1C_{1-6}$alkylthio, $R^3$ and $R^4$ each independently represent phenyl, pyridyl, pyrimidinyl, pyrazinyl or pyridazinyl, wherein each of said aromatic rings may optionally be substituted with one, two, three, four or five substituents each independently selected from hydroxy, halo, $C_{1-6}$alkyl, cyano, aminocarbonyl, polyhalo$C_{1-6}$alkyl, polyhalo$C_{1-6}$alkyloxy, polyhalo$C_{1-6}$alkylthio;

—X— is a bivalent radical selected from —NR$^{14}$—; —NH—NH—; —N=N—; —O—; —$C_{1-6}$alkanediyl-; —C(=O)—; —CHOH—; —S—; —S(=O)$_m$—;

each m independently is 1 or 2;

$R^{14}$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-4}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;

aryl is phenyl optionally substituted with one, two, three, four or five substituents each independently selected from hydroxy, halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;, Het$^1$ represents a monocyclic or bicyclic heterocycle selected from pyrrolyl, furanyl, thienyl, imidazolyl, oxazolyl, thiazolyl, pyridyl, pyrimidinyl, pyrazinyl, pyridazinyl, pyrrolidinyl, tetrahydrofuranyl, tetrahydrothienyl, imidazolidinyl, oxazolidinyl, thiazolidinyl, piperidinyl, hexahydropyrimidinyl, piperazinyl, hexahydropyridazinyl, benzopyrrolyl, benzofuranyl, benzothienyl, benzimidazolyl, benzoxazolyl, benzothiazolyl, quinolinyl, 2-oxo-1,2-dihydro-quinolinyl, each of said monocyclic or bicyclic heterocycle may optionally be substituted with one, two or three substituents each independently selected from halo, hydroxy, $C_{1-4}$alkyl, $C_{1-4}$alkyloxy, $C_{1-4}$alkylcarbonyl or polyhalo$C_{1-4}$alkyl;

Particular groups of compounds of formula (I) are those groups wherein one or more, preferably all, of the following conditions are met:

i) $R^1$ is hydrogen, $C_{1-6}$ alkyl or aryl$C_{1-6}$alkyl; or
ii) $R^2$ is hydrogen, $C_{1-6}$alkyl or arylthio; or
iii) $R^3$ is optionally substituted phenyl; or
iv) $R^4$ is optionally substituted phenyl; or
v) X is O, S or S(=O)$_m$.

Further particular compounds of formula (I) are those compounds wherein $R^1$ is hydrogen or wherein $R^1$ is $C_{1-3}$alkyl or aryl$C_{1-6}$alkyl, especially wherein $R^1$ is methyl.

Also particular compounds of formula (I) are those compounds wherein $R^2$ is hydrogen or $C_{1-6}$alkyl, especially methyl.

Still further interesting compounds of formula (I) are those compounds wherein $R^3$ or $R^4$ is phenyl substituted with one, two or three substituents selected from cyano, aminocarbonyl, $C_{1-6}$alkyl, halo, polyhalo$C_{1-6}$alkyl.

Yet further interesting compounds of formula (I) are those compounds wherein $R^4$ is phenyl substituted with cyano, aminocarbonyl, $C_{1-6}$alkyl, halo, polyhalomethyl, preferably cyano or aminocarbonyl. Preferred compounds of formula (I) are selected from:

4-[[3,4-dihydro-4-methyl-6-(2-methylphenoxy)-3-oxopyrazinyl]amino]-benzonitrile;

4-[[6-(2,4-dimethylphenoxy)-3,4-dihydro-4-methyl-3-oxopyrazinyl]amino]-benzonitrile;

4-[[3,4-dihydro-4-methyl-6-[(2-methylphenyl)thio]-3-oxopyrazinyl]amino]-benzonitrile;

3-[(4-chlorophenyl)amino]-1,6-dimethyl-5-(2-methylphenoxy)-2(1H)-pyrazinone;

5-(2,4-dimethylphenoxy)-1-methyl-3-(phenylamino)-2(1H)-pyrazinone;

3-[(4-chlorophenyl)amino]-5-[(2,4-dimethylphenyl)thio]-1,6-dimethyl-2(1H)-pyrazinone;

4-[[6-(2,4-dimethylphenoxy)-3,4-dihydro-3-oxo-4-(phenylmethyl)pyrazinyl]amino]-benzonitrile;

4-[[6-(2,4-dimethylphenoxy)-3,4-dihydro-3-oxo-4-(phenylmethyl)pyrazinyl]amino]-benzonitrile;

5-(2,4-dimethylphenoxy)-1-methyl-3-[[4-(trifluoromethyl)phenyl]amino]-2(1H)-pyrazinone;

5-(2,4-dimethylphenoxy)-1-methyl-3-[[4-(trifluoromethyl)phenyl]amino]-2(1H)-pyrazinone;

4-[[3,4-dihydro-4-methyl-3-oxo-6-[(2,4,6-trimethylphenyl)thio]pyrazinyl]amino]-benzonitrile;

3-[(4-chlorophenyl)amino]-1-methyl-5-[(2,4,6-trimethylphenyl)thio]-2(1H)-pyrazinone;

4-[[3,4-dihydro-4-methyl-3-oxo-6-[(2,4,6-trimethylphenyl)sulfonyl]pyrazinyl]amino]-benzonitrile;

4-[[6-[(2,4-dimethylphenyl)sulfonyl]-3,4-dihydro-4,5-dimethyl-3-oxopyrazinyl]amino]-benzonitrile;

4-[[3,4-dihydro-4,5-dimethyl-3-oxo-6-[(2,4,6-trimethylphenyl)sulfonyl]pyrazinyl]amino]-benzonitrile;

4-[[3,4-dihydro-4,5-dimethyl-3-oxo-6-[(2,4,6-trimethylphenyl)sulfonyl]pyrazinyl]amino]-benzonitrile;

4-[[3,4-dihydro-4,5-dimethyl-6-(2-methylphenoxy)-3-oxopyrazinyl]amino]-benzonitrile;

4-[[6-(2,4-dimethylphenoxy)-3,4-dihydro-4,5-dimethyl-3-oxopyrazinyl]amino]-benzonitrile;

4-[[6-[(2,4-dimethylphenyl)thio]-3,4-dihydro-4-methyl-3-oxopyrazinyl]amino]-benzonitrile;

3-[(4-chlorophenyl)amino]-5-(2,4-dimethylphenoxy)-1-methyl-2(1H)-pyrazinone;

3-[(4-chlorophenyl)amino]-5-(2,4-dimethylphenoxy)-1,6-dimethyl-2(1H)-pyrazinone;

4-[[3,4-dihydro-4,5-dimethyl-6-[(2-methylphenyl)thio]-3-oxopyrazinyl]amino]-benzonitrile;

3-[(4-chlorophenyl)amino]-5-(2,4-dimethylphenylthio)-1,6-dimethyl-2(1H)-pyrazinone;

4-[[6-[(4-cyanophenyl)amino]-4,5-dihydro-3,4-dimethyl-5-oxopyrazinyl]oxy]-3,5-dimethyl-benzonitrile;

4-[4,5-dimethyl-3-oxo-6-(2,4,6-trimethyl-phenylsulfanyl)-3,4-dihydro-pyrazin-2-ylamino]-benzonitrile;

4-[[6-[(2-methylphenyl)thio]-5-methyl-3,4-dihydro-3-oxo-4-(phenylmethyl)pyrazinyl]amino]-benzonitrile;

4-[[3,4-dihydro-5-methyl-6-[(2-methylphenyl)thio]-3-oxopyrazinyl]amino]-benzonitrile;

4-[[6-(2,4-dimethylphenoxy)-5-methyl-3,4-dihydro-3-oxo-4-(phenylmethyl)pyrazinyl]amino]-benzonitrile;
5-(2,4,6-trimethylphenoxy)-5-methyl-1-methyl-3-[[4-(trifluoromethyl)phenyl]amino]-2(1H)-pyrazinone;

their N-oxides, pharmaceutically acceptable addition salts, quaternary amines and stereochemically isomeric forms thereof.

Also preferred compounds of formula (I) are those compounds selected from
4-[[3,4-dihydro-4-methyl-6-(2-methylphenoxy)-3-oxopyrazinyl]amino]-benzonitrile;
4-[[6-(2,4-dimethylphenoxy)-3,4-dihydro-4-methyl-3-oxopyrazinyl]amino]-benzonitrile;
4-[[3,4-dihydro-4-methyl-6-[(2-methylphenyl)thio]-3-oxopyrazinyl]amino]-benzonitrile;
3-[(4-chlorophenyl)amino]-1,6-dimethyl-5-(2-methylphenoxy)-2(1H)-pyrazinone;
5-(2,4-dimethylphenoxy)-1-methyl-3-(phenylamino)-2(1H)-pyrazinone;
3-[(4-chlorophenyl)amino]-5-[(2,4-dimethylphenyl)thio]-1,6-dimethyl-2(1H)-pyrazinone;
4-[[6-(2,4-dimethylphenoxy)-3,4-dihydro-3-oxo-4-(phenylmethyl)pyrazinyl]amino]-benzonitrile,
4-[[6-(2,4-dimethylphenoxy)-3,4-dihydro-3-oxo-4-(phenylmethyl)pyrazinyl]amino]-benzonitrile;
5-(2,4-dimethylphenoxy)-1-methyl-3-[[4-(trifluoromethyl)phenyl]amino]-2(1H)-pyrazinone,
5-(2,4-dimethylphenoxy)-1-methyl-3-[[4-(trifluoromethyl)phenyl]amino]-2(1H)-pyrazinone,
4-[[3,4-dihydro-4-methyl-3-oxo-6-[(2,4,6-trimethylphenyl)thio]pyrazinyl]amino]-benzonitrile;
3-[(4-chlorophenyl)amino]-1-methyl-5-[(2,4,6-trimethylphenyl)thio]-2(1H)-pyrazinone,
4-[[3,4-dihydro-4-methyl-3-oxo-6-[(2,4,6-trimethylphenyl)sulfonyl]pyrazinyl]amino]-benzonitrile;
4-[[6-[(2,4-dimethylphenyl)sulfonyl]-3,4-dihydro-4,5-dimethyl-3-oxopyrazinyl]amino]-benzonitrile,
4-[[3,4-dihydro-4,5-dimethyl-3-oxo-6-[(2,4,6-trimethylphenyl)sulfonyl]pyrazinyl]amino]-benzonitrile;
4-[[3,4-dihydro-4,5-dimethyl-3-oxo-6-[(2,4,6-trimethylphenyl)sulfonyl]pyrazinyl]amino]-benzonitrile;
4-[[3,4-dihydro-4,5-dimethyl-6-(2-methylphenoxy)-3-oxopyrazinyl]amino]-benzonitrile,
4-[[6-(2,4-dimethylphenoxy)-3,4-dihydro-4,5-dimethyl-3-oxopyrazinyl]amino]-benzonitrile
4-[[6-[(2,4-dimethylphenyl)thio]-3,4-dihydro-4-methyl-3-oxopyrazinyl]amino]-benzonitrile;
3-[(4-chlorophenyl)amino]-5-(2,4-dimethylphenoxy)-1-methyl-2(1H)-pyrazinone;
3-[(4-chlorophenyl)amino]-5-(2,4-dimethylphenoxy)-1,6-dimethyl-2(1H)-pyrazinone;
4-[[3,4-dihydro-4,5-dimethyl-6[(2-methylphenyl)thio]-3-oxopyrazinyl]amino]-benzonitrile;
3-[(4-chlorophenyl)amino]-5-(2,4-dimethylphenylthio)-1,6-dimethyl-2(1H)-pyrazinone;
4-[[6-[(4-cyanophenyl)amino]-4,5-dihydro-3,4-dimethyl-5-oxopyrazinyl]oxy]-3,5-dimethyl-benzonitrile;
4-[4,5-dimethyl-3-oxo-6-(2,4,6-trimethyl-phenylsulfanyl)-3,4-dihydro-pyrazin-2-ylamino]-benzonitrile;

a N-oxide, a pharmaceutically acceptable addition salt, a quaternary amine and a stereochemically isomeric form thereof.

Especially preferred compounds of formula (I) are selected from
4-[[3,4-dihydro-4,5-dimethyl-6-(2-methylphenoxy)-3-oxopyrazinyl]amino]-benzonitrile;
4-[[6-(2,4-dimethylphenoxy)-3,4-dihydro-4,5-dimethyl-3-oxopyrazinyl]amino]-benzonitrile;
4-[[6-[(2,4-dimethylphenyl)thio]-3,4-dihydro-4-methyl-3-oxopyrazinyl]amino]-benzonitrile;
4-[[6-[(4-cyanophenyl)amino]-4,5-dihydro-3,4-dimethyl-5-oxopyrazinyl]oxy]-3,5-dimethyl-benzonitrile;

their N-oxides, pharmaceutically acceptable addition salts, quaternary amines and stereochemically isomeric forms thereof.

In general, the compounds of formula (I) may be prepared by reacting an intermediate of formula (II), wherein $W_1$ represents a suitable leaving group, such as a halogen atom, e.g. chloro, bromo and the like, with an intermediate of formula (III) in the presence of a suitable catalyst, such as for example CuCl, palladium acetate, palladium tetrakis (triphenylphosphine), a suitable base, such as for example $Cs_2CO_3$, and a suitable solvent, such as for example toluene or 1-methyl-2-pyrrolidinone, optionally in the presence of ethyl acetate only or combined with 2,4,6-(tri-tert-butyl)-phenol or optionally in the presence of naphtoic acid. Said reaction may preferably be performed at elevated temperatures and may optionally be performed under $N_2$ atmosphere.

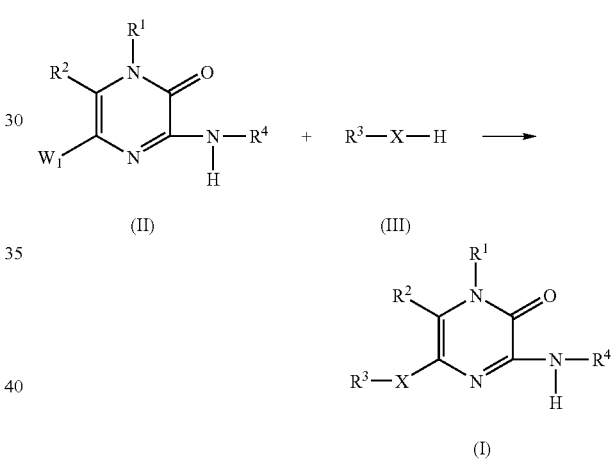

Compounds of formula (I) may be converted into each other following art-known functional group transformation reactions, comprising those described hereinafter.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I), wherein X represents S, said compounds being represented by formula (I-a), may be converted into a compound of formula (I), wherein X represents S(=O)$_m$, said compound being represented by formula (I-b), in the presence of a suitable oxidizing agent, such as a peroxide, for example, chloroperbenzoic acid, in the presence of a suitable solvent, such as for example dichloromethane.

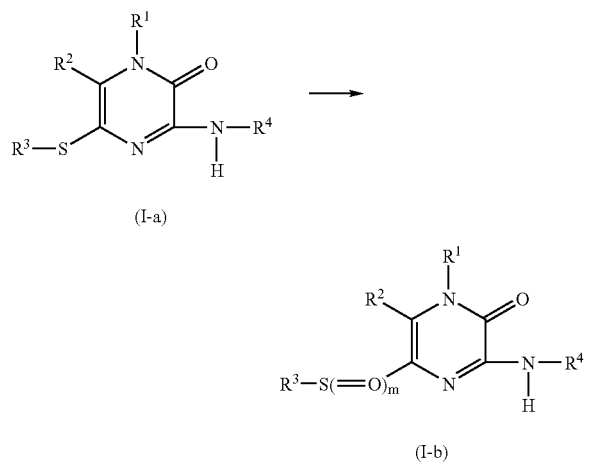

(I-a)

(I-b)

Compounds of formula (I), wherein R$^1$ is optionally substituted C$_{1-6}$alkyl, said R$^1$ being represented by R$^{1a}$ and said compounds being represented by formula (I-c), can be dealkylated to a compound of formula (I), wherein R$^1$ is hydrogen, said compound being represented by formula (I-d). Therefor, a compound of formula (I-c) is first dealkylated with a suitable agent, such as for example PO(W$_2$)$_3$, wherein W$_2$ represents a suitable leaving group, such as a halogen atom, for example chloro, resulting in the formation of an intermediate of formula (IV), with W$_2$ as defined above. Said intermediate of formula (IV) may subsequently be reacted with a suitable alcoholate, such as for example C$_{1-2}$alkylO$^-$Na$^+$, e.g. methanolate or ethanolate, in the presence of a suitable solvent, such as an alcohol, for example methanol, ethanol and the like, resulting in the formation of an intermediate of formula (V), which can be dealkylated into a compound of formula (I-d) by reaction with a suitable agent, such as for example BBr$_3$.

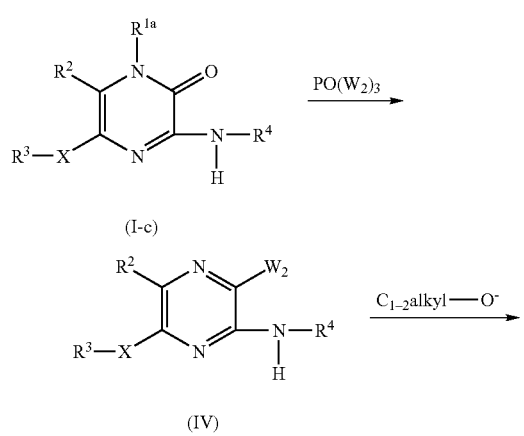

(I-c)

(IV)

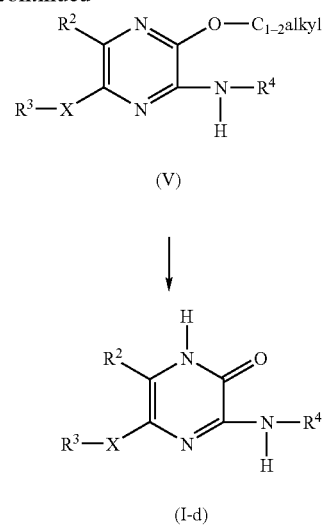

(V)

(I-d)

Compounds of formula (I-d) may also be prepared by deprotecting a compound of formula (I-c) wherein R$^{1a}$ is arylC$_{1-6}$alkyl, said compound being represented by formula (I-c-1), in the presence of a suitable agent, such as AlCl$_3$, and in the presence of a suitable solvent, such as for example o-dichlorobenzene. The reaction may be performed under N$_2$ atmosphere and at elevated temperatures.

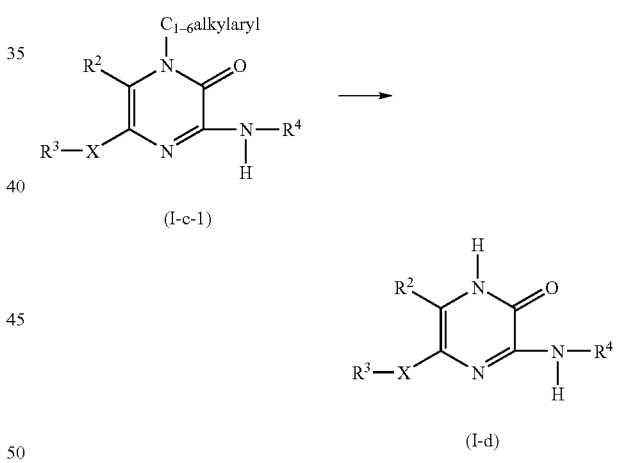

(I-c-1)

(I-d)

In the following paragraphs, there are described several methods of preparing the intermediates in the foregoing preparations. A number of intermediates and starting materials are commercially available or are known compounds which may be prepared according to conventional reaction procedures generally known in the art.

Intermediates of formula (II) can be prepared by reacting an intermediate of formula (VI) with an intermediate of formula (VII) in the presence of a suitable acid, such as for example a sulfonic acid, e.g. camphor sulfonic acid, trifluoromethane sulfonic acid and the like, and a suitable solvent, such as an alcohol, for example isopropanol and the like. Said reaction is preferably performed at elevated temperatures.

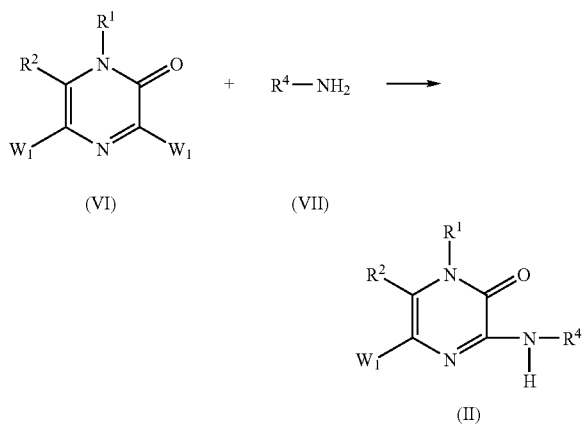

Intermediates of formula (VI) can be prepared by reacting an intermediate of formula (VIII), wherein $W_1$ is as defined above, with an intermediate of formula (IX), wherein $W_1$ is as defined above, in the presence of a suitable solvent, such as for example N,N-dimethylformamide, chlorobenzene, dichloromethane, chloroform, optionally in the presence of a suitable salt, such as for example tetraethylammonium bromide.

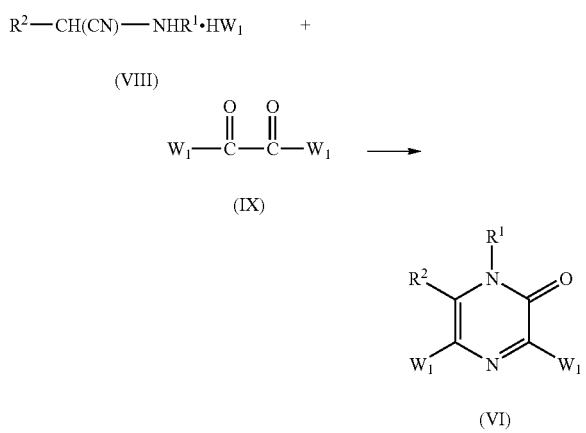

Intermediates of formula (VI), wherein $R^1$ is hydrogen, said intermediates being represented by formula (VI-a), can also be prepared by reacting an intermediate of formula (X) with a suitable halogenating agent, such as for example N-bromosuccinimide, in the presence of a suitable base, such as for example disodium carbonate, and a suitable solvent, such as for example N,N-dimethylformamide.

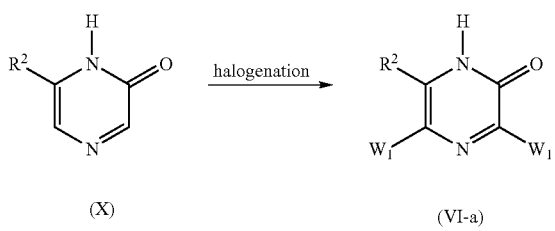

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) show antiretroviral properties, in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an everdecreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against multi drug resistant HIV strains, in particular multi drug resistant HIV-1 strains, more in particular the present compounds show activity against HIV strains, especially HIV-1 strains, that have acquired resistance to art-known non-nucleoside reverse transcriptase inhibitors. Art-known non-nucleoside reverse transcriptase inhibitors are those non-nucleoside reverse transcriptase inhibitors other than the present compounds. They also have little or no binding affinity to human α-1 acid glycoprotein.

Due to their antiretroviral properties, particularly their anti-HIV properties, especially their anti-HIV-1-activity, the compounds of formula (I), their N-oxides, pharmaceutically acceptable addition salts, quaternary amines and stereochemically isomeric forms thereof, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In view of the utility of the compounds of formula (I), there is provided a method of treating warm-blooded animals, including humans, suffering from or a method of preventing warm-blooded animals, including humans, to suffer from viral infections, especially HIV infections. Said method comprises the administration, preferably oral administration, of an effective amount of a compound of formula (I), a N-oxide form, a pharmaceutically acceptable addition salt, a quaternary amine or a possible stereoisomeric form thereof, to warm-blooded animals, including humans.

The present invention also provides compositions for treating viral infections comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols (e.g. polyethylene glycols), oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD)

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (I) and the water-soluble polymer, wherein one component is dispersed more or less evenly throughout the other component or components ( in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermo-dynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps:
a) dissolving the compound of formula (I) and the water-soluble polymer in an appropriate solvent, optionally at elevated temperatures;
b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:
a) mixing a compound of formula (I) and an appropriate water-soluble polymer,
b) optionally blending additives with the thus obtained mixture,
c) heating and compounding the thus obtained blend until one obtains a homogenous melt,
d) forcing the thus obtained melt through one or more nozzles; and
e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 μm, preferably less than 400 μm and most preferably less than 125 μm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the through-put rate in the melt-extruder.

The water-soluble polymers in the particles are polymers that have an apparent viscosity, when dissolved at 20° C. in an aqueous solution at 2% (w/v), of 1 to 5000 mPa.s more preferably of 1 to 700 mPa.s, and most preferred of 1 to 100 mPa.s. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α-, β-, γ-cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

Of particular utility are the β-cyclodextrin ethers, e.g. dimethyl-β-cyclodextrin as described in Drugs of the Future, Vol. 9, No. 8, p. 577–578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another type of substituted cyclodextrins are sulfobutyl-cyclodextrines.

The ratio of the compound of formula (I) over the water soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) and optionally a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (I) can be used alone or in combination with other therapeutic agents, such as anti-virals, antibiotics, antifungals, immunomodulators or vaccines for the treatment of viral infections and opportunistic infections. They may also be used alone or in combination with other prophylactic agents for the prevention of viral infections. The present compounds may be used in vaccines and methods for protecting individuals against viral infections over an extended period of time. The present compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of an antiretroviral compound and a compound of formula (I) can be used as a medicine. Thus, the present invention also relates to a product containing (a) a compound of formula (I), and (b) another antiretroviral compound, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as suramine, pentamidine, thymopentin, castanospermine, dextran (dextran sulfate), foscarnet-sodium (trisodium phosphono formate); nucleoside reverse transcriptase inhibitors, e.g. zidovudine (3'-azido-3'-deoxythymidine, AZT), didanosine (2',3'-dideoxyinosine; ddI), zalcitabine (dideoxycytidine, ddC) or lamivudine (2'-3'-dideoxy-3'-thiacytidine, 3TC), stavudine (2',3'-didehydro-3'-deoxythymidine, d4T), abacavir and the like; non-nucleoside reverse transciptase inhibitors such as nevirapine (11-cyclopropyl-5,11-dihydro-4-methyl-6H-dipyrido-[3,2-b:2',3'-e][1,4]diazepin-6-one), efavirenz, delavirdine, TMC-120, TMC-125 and the like; compounds of the TIBO (tetrahydroimidazo[4,5,1-jk][1,4]-benzodiazepine-2(1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2(1H)-thione; compounds of the α-APA (α-anilino phenyl acetamide) type e.g. α-[(2-nitrophenyl)amino]-2,6-dichlorobenzene-acetamide and the like; inhibitors of transactivating proteins, such as TAT-inhibitors, e.g. RO-5-3335, or REV inhibitors, and the like; protease inhibitors e.g. indinavir, ritonavir, saquinavir, lopinavir (ABT-378), nelfinavir, amprenavir, TMC-126, BMS-232632, VX-175 and the like; fusion inhibitors, e.g. T-20, T-1249 and the like; CXCR4 receptor antagonists, e.g. AMD-3100 and the like; inhibitors of the viral integrase; nucleotide-like reverse transcriptase inhibitors, e.g. tenofovir and the like; ribonucleotide reductase inhibitors, e.g. hydroxyurea and the like. By administering the compounds of the present invention with other anti-viral agents which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional anti-retroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compounds of the present invention may also be administered in combination with immunomodulating agents, e.g. levamisole, bropirimine, anti-human alpha interferon antibody, interferon alpha, interleukin 2, methionine enkephalin, diethyldithiocarbamate, tumor necrosis factor, naltrexone and the like; antibiotics, e.g. pentamidine isethiorate and the like; or cholinergic agents, e.g. tacrine, rivastigmine, donepezil, galantamine and the like to prevent or combat infection and diseases or symptoms of diseases associated with HIV infections, such as AIDS and ARC, e.g. dementia. A compound of formula (I) can also be combined with another compound of formula (I).

Although the present invention focuses on the use of the present compounds for preventing or treating HIV infections, the present compounds may also be used as inhibitory agents for other viruses which depend on similar reverse transcriptases for obligatory events in their life cycle.

Experimental Part

A. Preparation of the Intermediate Compounds

EXAMPLE A1 a. A solution of oxalyl bromide (8.82 g) in $CH_2Cl_2$ (50 ml) was added dropwise to a suspension of 2-(methylamino)-propanenitrile hydrobromide (3.30 g) in dichloromethane (200 ml). After addition, 3 drops of N,N-dimethylformamide were added and the resulting mixture was immediately refluxed for 24 hours. After evaporation of the solution, the residue was purified by column chromatography (silica gel, 5% ethyl acetate in dichloromethane), yielding 3.90 g (69%) of 3,5-dibromo-1,6-dimethyl-2 (1H)-pyrazinone (interm. 1; m.p. 119–120° C.).

b. Methylaminoacetonitrile hydrochloride [CAS-25808-30-4] (43.91 g, 400 mmol) was treated with 150 ml of an aqueous solution of $K_2CO_3$ (55.28 g, 400 mmol). This aqueous solution was extracted with $CH_2Cl_2$ (4×150 ml). The dichloromethane solution was dried over $MgSO_4$ and evaporated at 15–18° C. under reduced pressure. The residue was dissolved in dry $Et_2O$ and HBr gas was bubbled through the solution. The precipitate was collected by filtration and dried overnight in a dessicator, yielding 32.62 g (54%) of methylaminoacetonitrile hydrobromide (interm. 2a).

c. Preparation of intermediate 2

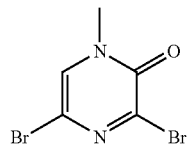

Oxalyl bromide (3.90 ml, 2.62 mmol) was added dropwise to a suspension of intermediate 2a (2 g, 13.31 mmol) in $CHCl_3$ (50 ml), followed by addition of tetraethylammonium bromide (1.45 g, 6.65 mmol). The reaction mixture was refluxed for 4 hours and then evaporated. The residue was chromatographed on a silica gel column (10% ethyl acetate in $CH_2Cl_2$), yielding 0.99 g (28%) of intermediate 2b ([MH+]=mass of the protonated compound determined by chemical ionization mass spectrometry=267).

EXAMPLE A2 a. A mixture of intermediate 1 (1.50 g), 4-aminobenzonitrile (0.94 g), and camphorsulfonic acid (1.26 g) in 2-propanol (50 ml) was refluxed (oil bath 120° C.) for 48 hours. After cooling of the reaction mixture, the precipitate was collected by filtration and successively washed with 2-propanol, aqueous potassium carbonate, water and diethyl ether. Purification by column chromatography on silica gel (5% ethyl acetate in $CH_2Cl_2$) afforded 1.42 g of 5-bromo-3-(4-cyanophenylamino)-1,6-dimethyl-2(1H)-pyrazinone (interm. 3; m.p. 254–255° C.).

b. Preparation of intermediate 4

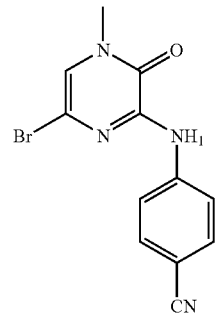

A mixture of intermediate 2b (1.34 g; 5 mmol), 4-aminobenzonitrile (0.904 g; 7.5 mmol), and 10-camphorsulfonic acid (1.18 g; 5 mmol) in 2-propanol (50 ml) was refluxed (oil bath 120° C.) for 48 hours. After cooling of the reaction mixture, the precipitate was collected by filtration and successively washed with 2-propanol, aqueous potassium carbonate, water, and diethyl ether. Purification by column chromatography on silica gel (10% ethyl acetate in $CH_2Cl_2$) afforded 1.21 g (79%) of intermediate 4; m.p. 293–294° C.).

EXAMPLE A3 a. Preparation of intermediate 5

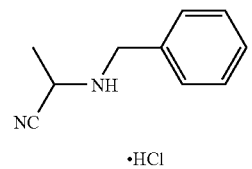

To a mixture of 19 g (100 mmol) of $Na_2S_2O_3$ and 8.81 g (200 mmol) of acetaldehyde in 400 ml of water was added 21.4 g (200 mmol) of benzylamine. After stirring for 4 hours at 60° C., the reaction mixture was cooled to room temperature followed by addition of 13.03 g of KCN. This reaction mixture was stirred again at 60° C. for 15 hours. It was then extracted (2×250 ml) with $CH_2Cl_2$ and the organic layer was washed with water, dried over $MgSO_4$, filtered and evaporated. The resulting α-aminonitrile was dissolved in 300 ml of diethyl ether. HCl gas was bubbled through the solution for 15 minutes at 0° C. The resulting α-aminonitrile hydrochloride was filtered. The precipitate was washed with diethyl ether and dried under vacuum, yielding 16.63 g (85%) of intermediate 5.

b. Preparation of intermediate 6

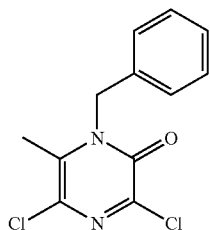

Chlorobenzene (20 ml) was added at room temperature to intermediate 5 (16.63 g; 85 mmol) followed by dropwise addition of a solution of oxalyl chloride (43 ml, 480 mmol) in 100 ml of chlorobenzene over 30 minutes, and 10 g of triethylammonium chloride. The reaction mixture was stirred at room temperature for 2 days under nitrogen. After evaporation of the solvent, the residue was purified by silica gel column chromatography (using $CH_2Cl_2$ and 5% ethyl acetate in $CH_2Cl_2$ as eluent). Recrystallisation in EtOH afforded 14.41 g (63%) of intermediate 6.

c. Preparation of intermediate 7

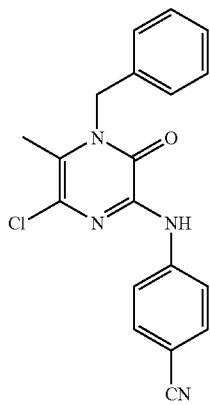

A mixture of intermediate 6 (1.35 g; 5 mmol), 4-aminobenzonitrile (0.904 g; 7.5 mmol), and 10-camphorsulfonic acid (1.18 g; 5 mmol) in 2-propanol (50 ml) was refluxed (oil bath 120° C.) for 48 hours. After cooling of the reaction mixture, the precipitate was collected by filtration and successively washed with 2-propanol, aqueous potassium carbonate, water, and diethyl ether. Purification by column chromatography on silica gel (5% ethyl acetate in $CH_2Cl_2$) afforded 80% of intermediate 7 (m.p. 254° C.).

EXAMPLE A4 a. Preparation of intermediate 8

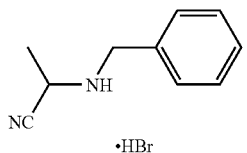

To a solution of dl-lactonitrile (2.243 g; 30 mmol) in toluene, benzylamine (3.226 g; 30 mmol) was added. After stirring at room temperature over night, the water formed was removed and the toluene solution was dried over $MgSO_4$. After filtration and evaporation of toluene, the resulting residue was dissolved in dry ethyl ether and treated with hydrogen bromide at 0° C. for 30 minutes. The resulting bromide salt was filtered and dried, yielding 6.87 g (95%) of intermediate 8.

b. Preparation of intermediate 9

A solution of oxalyl bromide (60 ml; 40 mmol) in $CH_2Cl_2$ (50 ml) was added dropwise to a suspension of intermediate 8 (4.82 g; 20 mmol) in $CH_2Cl_2$ (200 ml). After addition, a few drops (3) of N,N-dimethylformamide were added and the resulting mixture was immediately refluxed for 24 hours. After evaporation of the solution, the residue was purified by column chromatography on silica gel (5% ethyl acetate in $CH_2Cl_2$). After recrystallisation in EtOH, 4.30 g (60%) of intermediate 9 was obtained (m.p. 126° C.).

c. Preparation of intermediate 10

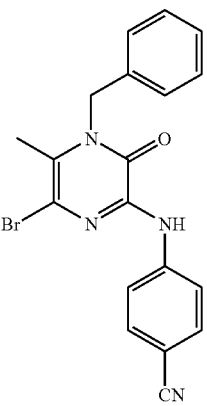

A mixture of intermediate 9 (1.79 g; 5 mmol), 4-aminobenzonitrile (0.904 g; 7.5 mmol), and 10-camphorsulfonic acid (1.18 g; 5 mmol) in 2-propanol (50 ml) was refluxed (oil bath 120° C.) for 48 hours. After cooling of the reaction mixture, the precipitate was collected by filtration and successively washed with 2-propanol, aqueous potassium carbonate, water, and diethyl ether. Purification by column chromatography on silica gel (eluent: $CH_2Cl_2$) afforded 1.80 g (91%) of intermediate 10 (m.p. 262° C.).

B. Preparation of the Final Compounds

EXAMPLE B1 a. Preparation of compound 26

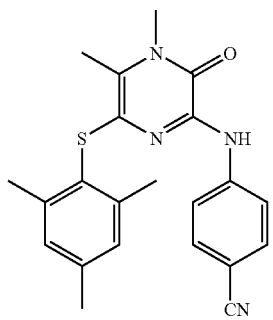

A mixture of intermediate 3 (prepared according to A2.a) (0.32 g), 2,4,6-trimethylbenzenethiol (0.304 g), cesium carbonate (0.655 g), copper (I) chloride (0.060 g) and 5 drops of ethyl acetate in toluene (50 ml) was heated at 120° C. for 24 hours. After evaporation of the solvent, the residue was purified by column chromatography (silica gel, 40% hexane ii ethyl acetate). The resulting product was repurified by column chromatography (1/1 mixture of hexane and ethyl acetate; 40% hexane in ethyl acetate), yielding 129 mg of comp. 26. (m.p. 226–227° C.).

b. Preparation of compound 20

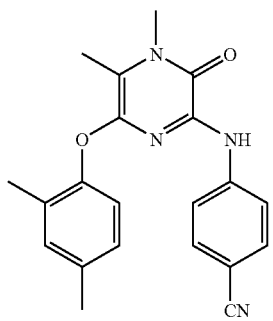

A mixture of intermediate 3 (prepared according to A2a) (2.393 g; 7.5 mmol), 2,4-dimethylphenol (1.887 g; 15 mmol), 2,4,6-tri-tert-butylphenol (2.026 g; 7.5 mmol), cesium carbonate (7.536 g; 23 mmol), copper (I) chloride (150 mg), and ethyl acetate (1 ml) in toluene (500 ml) was heated at 120° C. for 24 hours. After evaporation of the solvent, the residue was purified by column chromatography (silica gel, 10% ethyl acetate in CH$_2$Cl$_2$) followed by high performance liquid chromatography (40% hexanes in ethyl acetate) to give 0.945 g (35%) of compound 20.

c. Preparation of compound 1

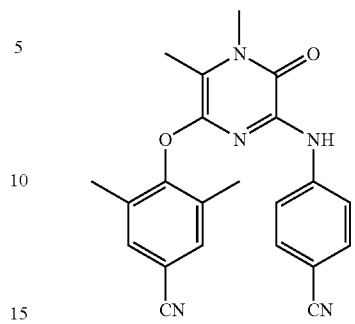

A mixture of intermediate 3 (prepared according to A2.a) (0.24 g; 0.75 mmol), 4-hydroxy-3,5-dimethylbenzonitrile (0.22 g; 1.5 mmol), cesium carbonate (0.344 g; 1.05 mmol), copper (I) chloride (0.04 g), 1-naphtoic acid (0.18 g; 1.05 mmol) and molecular sieves 4 Å (0.20 g) was refluxed in toluene (30 ml) for 6 days. After evaporation of the solvent, the residue was purified by column chromatography (silica gel, 15% ethyl acetate in CH$_2$Cl$_2$) followed high performance liquid chromatography (40% hexanes in ethyl acetate) to give 28 mg of compound 1.

EXAMPLE B2

Preparation of compound 17 and compound 18

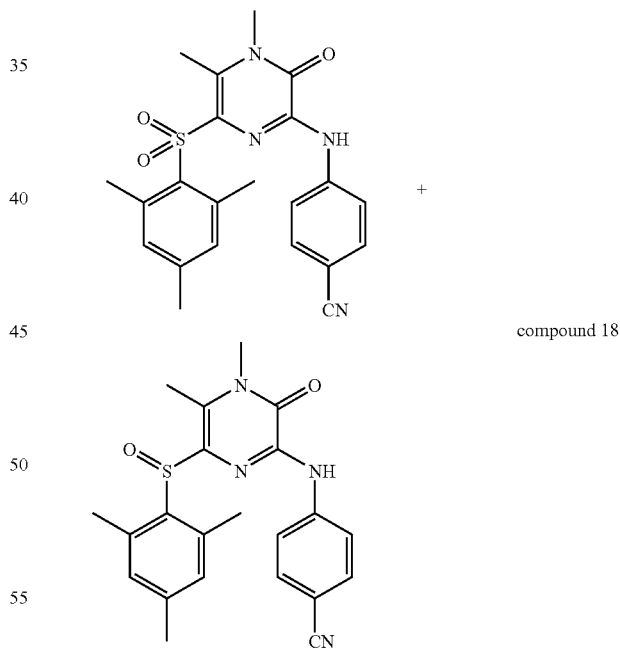

To a solution of compound 26 (0.101 g) in 15 ml CH$_2$Cl$_2$, was added 3-chloroperbenzoic acid (0.082 g). After 24 hours of stirring at room temperature, the reaction mixture was washed with an aqueous solution of potassium carbonate and dried before evaporation. Column chromatography was performed on the residue eluting first compound 17 with 10% ethyl acetate in CH$_2$Cl$_2$ and then compound 18 with ethyl acetate, yielding 0.033 g of compound 17 and 0.058 g of compound 18.

EXAMPLE B3 a. Preparation of compound 27

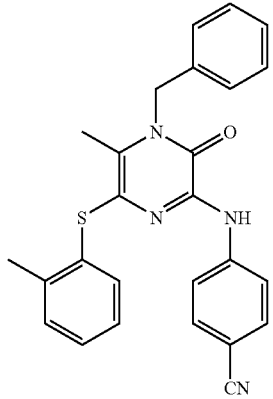

To a dry two-neck round flask under $N_2$ was added intermediate 7 (prepared according to A3.c) (2 mmol), dry 1-methyl-2-pyrrolidinone (10 ml) and freshly thiocresol (0.523 g; 4 mmol). The solid $Cs_2CO_3$ (1.638 g; 5 mmol) was then added under $N_2$. The flask was then heated in an oil bath at 130° C. for 3 hours while the contents of the flask were stirred. After cooling to room temperature, the solvent was evaporated under reduced pressure. Water was added to the residue and extracted three times with $CH_2Cl_2$. The collected $CH_2Cl_2$ was washed with brine and dried over $MgSO_4$. After filtration and removal of organic solvent, the crude products were purified by column chromatography (silica gel, eluent 5% ethyl acetate in $CH_2Cl_2$-10% ethyl acetate in $CH_2Cl_2$), yielding 0.525 g (60%) of compound 27 (m.p. 195° C.).

b. Preparation of compound 28

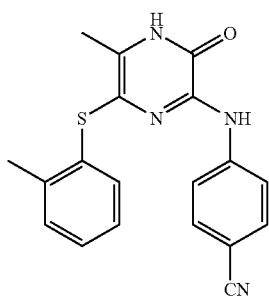

0.438 g (1 mmol) of compound 27 was added to dry o-dichlorobenzene under $N_2$ followed by addition of 0.134 g (3 mmol) of $AlCl_3$. The flask was then heated in an oil bath at 160° C. for 6 hours while the contents of the flask were stirred. After cooling to room temperature, the solvent was evaporated under reduced pressure. The residue was washed with water and dried under vacuum. Crystallisation by using ethyl acetate yielded 0.104 g (30%) of compound 28 (m.p. 290–291° C.).

EXAMPLE B4

Preparation of compound 9

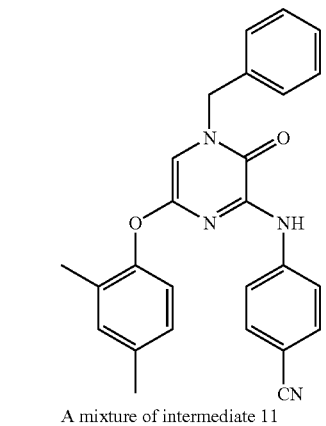

A mixture of intermediate 11

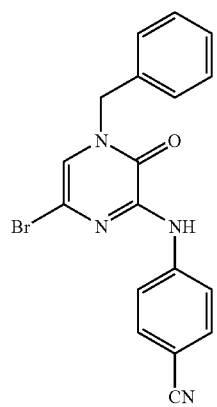

(prepared according to A4.c)

(0.381 g; 1 mmol), 2,4-dimethylphenol (0.252 g; 2 mmol), cesium carbonate (0.819 g; 2.5 mmol), and catalytic amounts of copper (I) chloride (50 mg) in toluene (60 ml) was heated at 110° C. for 48 hours. After cooling to room temperature, the solvent was evaporated and the crude mixture was extracted with $CH_2Cl_2$ (three times). The organic phase was dried over $MgSO_4$, filtered and evaporated. The residue was purified by column chromatography (silica gel, 2–5% ethyl acetate in $CH_2Cl_2$) followed by high performance liquid chromatography (2% ethyl acetate in $CH_2Cl_2$), yielding 0.53 g (12.5%) of compound 9 (m.p. 175° C.).

EXAMPLE B5

Preparation of compound 4 and compound 5

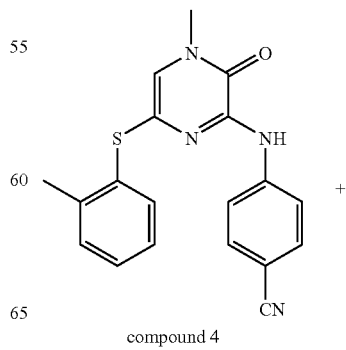

compound 4

+

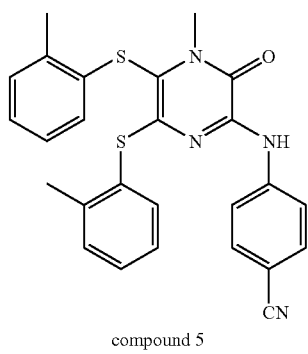
compound 5

A mixture of intermediate 4 (prepared according to A2.b) (230 mg, 0.75 mmol), o-thiocresol (145 mg, 1.13 mmol), cesium carbonate (494 mg, 1.51 mmol) and copper (I) chloride (30 mg) in toluene (25 ml) was heated at 120° C. for 36 hours. After cooling to room temperature, the solvent was evaporated and the residue was extracted with $CH_2Cl_2$. The organic phase was dried over $MgSO_4$, filtered and evaporated. After column chromatography of the residue on silica gel (5% ethyl acetate in $CH_2Cl_2$), two impure fractions were obtained. The first fraction was further purified by recrystallisation in ethyl acetate, yielding 0.071 g (20%) of compound 5. The second fraction was further purified by high performance liquid chromatography on silica gel (hexanes/ethyl acetate: 2/3), yielding 0.078 g (30%) of compound 4.

Table 1 lists the compounds of formula (I) which were prepared according to one of the above examples.

TABLE 1

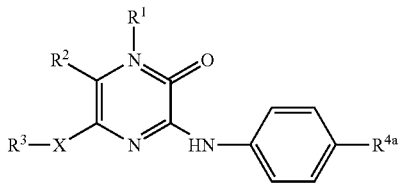

| Comp No. | Ex. No. | R¹ | R² | R³ | R⁴ᵃ | X | Physical data |
|---|---|---|---|---|---|---|---|
| 1 | B1c | CH₃ | CH₃ | 4-cyano-2,6-dimethyl-phenyl | C≡N | O | 114–150° C. |
| 2 | B1a | CH₃ | H | 2-methyl-phenyl | C≡N | O | 202–204° C. |
| 3 | B1a | CH₃ | H | 2,4-dimethyl-phenyl | C≡N | O | 200.5–202° C. |
| 4 | B5 | CH₃ | H | 2-methyl-phenyl | C≡N | S | 242.7–243.5° C. |
| 5 | B5 | CH₃ | (2-methylphenyl-S—) | 2-methyl-phenyl | C≡N | S | 266.8–267.4° C. |
| 6 | B1b | CH₃ | CH₃ | 2-methyl-phenyl | Cl | O | 222° C. |
| 7 | B1b | CH₃ | H | 2,4-dimethyl-phenyl | H | O | 166–166.5° C. |
| 8 | B1a | CH₃ | CH₃ | 2,4-dimethyl-phenyl | Cl | S | 213° C. |
| 9 | B4 | (benzyl) | H | 2,4-dimethyl-phenyl | C≡N | O | 175° C. |
| 10 | B4 | (benzyl) | H | 2-methyl-phenyl | C≡N | O | 199° C. |
| 11 | B1b | CH₃ | H | 2,4-dimethyl-phenyl | CF₃ | O | 147–148° C. |
| 12 | B1b | CH₃ | H | 2,4-dimethyl-phenyl | F | O | 151–152° C. |
| 13 | B1a | CH₃ | H | 2,4,6-trimethyl-phenyl | C≡N | S | 273–275° C. |
| 14 | B1a | CH₃ | H | 2,4,6-trimethyl-phenyl | Cl | S | 224–225° C. |

TABLE 1-continued

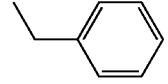

| Comp No. | Ex. No. | $R^1$ | $R^2$ | $R^3$ | $R^{4a}$ | X | Physical data |
|---|---|---|---|---|---|---|---|
| 15 | B2 | $CH_3$ | H | 2,4,6-trimethyl-phenyl | C≡N | $S(=O)_2$ | 313–314° C. |
| 16 | B2 | $CH_3$ | $CH_3$ | 2,4-dimethyl-phenyl | C≡N | $S(=O)_2$ | 294–296° C. |
| 17 | B2 | $CH_3$ | $CH_3$ | 2,4,6-trimethyl-phenyl | C≡N | $S(=O)_2$ | 282–284° C. |
| 18 | B2 | $CH_3$ | $CH_3$ | 2,4,6-trimethyl-phenyl | C≡N | $S(=O)$ | 239–240° C. |
| 19 | B1b | $CH_3$ | $CH_3$ | 2-methyl-phenyl | C≡N | O | 236° C. |
| 20 | B1b | $CH_3$ | $CH_3$ | 2,4-dimethyl-phenyl | C≡N | O | 208° C. |
| 21 | B1a | $CH_3$ | H | 2,4-dimethyl-phenyl | C≡N | S | 231–232° C. |
| 22 | B1a | $CH_3$ | H | 2,4-dimethyl-phenyl | Cl | O | 180–181° C. |
| 23 | B1b | $CH_3$ | $CH_3$ | 2,4-dimethyl-phenyl | Cl | O | 214° C. |
| 24 | B1a | $CH_3$ | $CH_3$ | 2-methyl-phenyl | C≡N | S | 240° C. |
| 25 | B1b | $CH_3$ | $CH_3$ | 2,4,6-trimethyl-phenyl | Cl | O | [MH+] = 374* |
| 26 | B1a | $CH_3$ | $CH_3$ | 2,4,6-trimethyl-phenyl | C≡N | S | 226–227° C. |
| 27 | B3a | 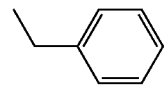 | $CH_3$ | 2-methyl-phenyl | C≡N | S | 195° C. |
| 28 | B3b | H | $CH_3$ | 2-methyl-phenyl | C≡N | S | 290–291° C. |
| 29 | B1b | 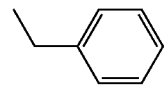 | $CH_3$ | 2,4-dimethyl-phenyl | C≡N | O | 147–149° C. |
| 30 | B1b | $CH_3$ | $CH_3$ | 2,4,6-trimethyl-phenyl | $CF_3$ | O | [MH+] = 418* |

*[MH+] is the mass of the protonated compound

C. Pharmacological Example

The pharmacological activity of the present compounds was examined using the following test.

A rapid, sensitive and automated assay procedure was used for the in vitro evaluation of anti-HIV agents. An HIV-1 transformed T4-cell line, MT-4, which was previously shown (Koyanagi et al., *Int. J. Cancer*, 36, 445–451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration ($CC_{50}$ in μM) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \quad \text{expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($IC_{50}$ in μM). The ratio of $CC_{50}$ to $IC_{50}$ was defined as the selectivity index (SI). The compounds of formula (I) were shown to inhibit HIV-1 effectively. Particular $IC_{50}$, $CC_{50}$ and SI values are listed in Table 2 hereinbelow.

TABLE 2

| Co. No. | IC$_{50}$ (μM) | CC$_{50}$ (μM) | SI |
|---|---|---|---|
| 1 | 0.0063 | 99.8 | 15849 |
| 2 | 0.0040 | 100.5 | 25119 |
| 3 | 0.0006 | 95.1 | 158489 |
| 4 | 0.02 | 100.2 | 5012 |
| 6 | 0.100 | 100 | 1000 |
| 7 | 0.1995 | 99.9 | 501 |
| 8 | 0.501 | 100.2 | 200 |
| 9 | 0.0316 | 99.9 | 3162 |
| 10 | 0.316 | 99.9 | 316 |
| 11 | 0.501 | 100.2 | 200 |
| 13 | 0.0158 | 99.7 | 6310 |
| 14 | 0.0794 | 99.9 | 1259 |
| 15 | 0.0079 | 99.4 | 12589 |
| 16 | 0.0316 | 99.9 | 3162 |
| 17 | 0.0050 | 99.8 | 19953 |
| 18 | 0.0040 | 100.5 | 25119 |
| 19 | 0.0050 | 99.8 | 19953 |
| 20 | 0.0025 | 99.5 | 39811 |
| 21 | 0.0050 | 99.8 | 19953 |
| 22 | 0.020 | 100.24 | 5012 |
| 23 | 0.0501 | 99.9 | 1995 |
| 24 | 0.0251 | 99.9 | 3981 |

The invention claimed is:

1. A compound of formula

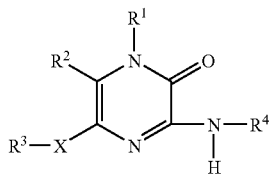

(I)

a N-oxide, a pharmaceutically acceptable addition salt, a quaternary amine or a stereochemically isomeric form thereof, wherein $R^1$ is hydrogen, hydroxy, cyano, amino, mono- or di($C_{1-4}$alkyl)amino, formyl, carboxyl, $C_{1-6}$alkyl, hydroxy$C_{1-6}$alkyl, polyhalo$C_{1-6}$alkyl, $C_{2-6}$alkenyl, $C_{2-6}$alkynyl, $C_{3-7}$cycloalkyl, $C_{1-6}$alkyloxy, $C_{1-6}$alkylcarbonyl, aminocarbonyl, —S(=O)$_m$—NH$_2$, mono- or di($C_{1-4}$alkyl)aminocarbonyl, $C_{1-6}$alkyloxycarbonyl, $C_{1-6}$alkylcarbonyloxy, aryl, aryl$C_{1-6}$alkyl or aryloxy;

$R^2$ is hydrogen; halo; mercapto; formyl; cyano; carboxyl; azido; hydroxy; oxiranyl; amino; mono- or di($C_{1-4}$alkyl)amino; formylamino; $R^5R^6N$—C(=O)—; $R^7$—N=C($R^8$)—; $C_{1-6}$alkyl-S(=O)$_m$; aryl-S(=O)$_m$; $C_{2-6}$alkenyl optionally substituted with one or two substituents each independently selected from halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, N-hydroxy-imino, aryl or Het$^1$; $C_{2-6}$alkynyl optionally substituted with one or two substituents each independently selected from halo, hydroxy, cyano, formyl, $C_{1-6}$alkyloxy, $C_{1-6}$alkylcarbonyl, $C_{1-6}$alkyloxycarbonyl, $C_{1-6}$alkylcarbonyloxy, N-hydroxy-imino, aryl or Het$^1$; $C_{1-6}$alkyloxy; hydroxy$C_{1-6}$alkyloxy; amino$C_{1-6}$alkyloxy; mono- or di($C_{1-4}$alkyl)amino-$C_{1-6}$alkyloxy; $C_{1-6}$alkylcarbonyl; arylcarbonyl; Het$^1$carbonyl; $C_{1-6}$alkyloxycarbonyl; $C_{1-6}$alkylcarbonyloxy; aryl; aryloxy; aryl$C_{1-6}$alkyloxy; arylthio; aryl$C_{1-6}$alkylthio; mono- or di(aryl)amino; Het$^1$; Het$^1$oxy; Het$^1$thio; Het$^1C_{1-6}$alkyloxy; Het$^1C_{1-6}$alkylthio; mono- or di(Het$^1$)amino; $C_{3-7}$cycloalkyl; $C_{3-7}$cycloalkyloxy; $C_{3-7}$cycloalkylthio; $C_{1-6}$alkylthio; hydroxy$C_{1-6}$alkylthio; amino$C_{1-6}$alkylthio; mono- or di($C_{1-4}$alkyl)amino$C_{1-6}$alkylthio; $C_{1-6}$alkyl optionally substituted with one, two or three substituents each independently selected from halo, hydroxy, cyano, $C_{1-6}$alkyloxy, $C_{1-6}$alkylthio, hydroxy-$C_{1-6}$alkyloxy, $C_{1-6}$alkyloxy$C_{1-6}$alkyloxy, $C_{1-6}$alkylcarbonyl, $C_{1-6}$alkylcarbonyl-oxy, aminocarbonyloxy, mono- or di($C_{1-4}$alkyl)aminocarbonyloxy, $C_{1-6}$alkyloxycarbonyl, $C_{1-6}$alkyloxycarbonyl-$C_{1-6}$alkyloxy, $C_{1-6}$alkyloxycarbonyl$C_{1-6}$alkylthio, aryl, Het$^1$, aryloxy, arylthio, aryl$C_{1-6}$alkyloxy, aryl$C_{1-6}$alkylthio, Het$^1C_{1-6}$alkyloxy, Het$^1C_{1-6}$alkylthio, $C_{1-6}$alkyl-S(=O)$_m$-oxy, amino, mono- or di($C_{1-6}$alkyl)amino, formylamino, $C_{1-6}$alkyloxycarbonylamino, $C_{1-6}$alkyloxy$C_{1-6}$alkylcarbonylamino, mono- or di(aryl)amino, mono- or di(aryl$C_{1-4}$alkyl)amino, ($C_{1-6}$alkyl)(aryl$C_{1-4}$alkyl)amino, mono- or di($C_{1-4}$alkyloxy$C_{1-4}$alkyl)amino, mono- or di(aryl$C_{1-4}$alkyloxy$C_{1-4}$alkyl)amino, mono- or di($C_{1-4}$alkylthio$C_{1-4}$alkyl)amino, mono- or di(aryl$C_{1-4}$alkylthio$C_{1-4}$alkyl)amino, mono- or di(Het$^1C_{1-4}$alkyl)amino, mono- or di($C_{1-4}$alkyl)amino$C_{1-4}$alkyloxy, mono- or di($C_{1-4}$alkyl)amino$C_{1-4}$alkylthio, $R^9$—C(=O)—NH—, $R^{10}$—NH—C(=O)—NH—, $R^{11}$—S(=O)$_2$—NH—, or a radical of formula

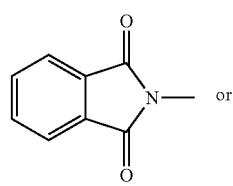

(a-1)

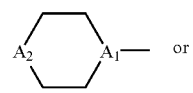

(a-2)

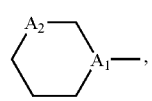

(a-3)

with $A_1$ representing CH or N, and $A_2$ representing CH$_2$, NR$^{12}$ or O, provided that when $A_1$ is CH then $A_2$ is other than CH$_2$, said radical of formula (a-1), (a-2) or (a-3) optionally being substituted with one or two substituents each independently selected from hydrogen, $C_{1-6}$alkyl, $C_{1-6}$alkyloxy, hydroxy$C_{1-4}$alkyl, $C_{1-6}$alkyloxycarbonyl, $C_{1-6}$alkyloxycarbonyl-$C_{1-4}$alkyl, amino$C_{1-6}$alkyl, carbonyl, hydroxy, cyano, amide, mono- or di($C_{1-4}$alkyl)aminocarbonyl, mono- or di($C_{1-4}$alkyl)amino$C_{1-6}$alkyl, 4-hydroxy-phenyl, 4-cyano-phenyl;

$R^3$ and $R^4$ each independently represent phenyl, pyridyl, pyrimidinyl, pyrazinyl or pyridazinyl, wherein each of said aromatic rings may optionally be substituted with one, two, three, four or five substituents each independently selected from hydroxy, halo, $C_{1-6}$alkyl optionally substituted with cyano or —C(=O)R$^{13}$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, aminocarbonyl, nitro, amino, mono- or di($C_{1-6}$alkyl)amino, polyhalo$C_{1-6}$alkyl, polyhalo$C_{1-6}$alkyloxy, polyhalo$C_{1-6}$alkylthio, —S(=O)$_p$R$^{13}$, —NH—S(=O)$_p$R$^{13}$, —C(=O)R$^{13}$, —NHC(=O)H, —C(=O)NHNH$_2$, —NHC(=O)R$^{13}$, —C(=NH)R$^{13}$ or a radical of formula

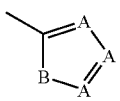
(b)

wherein each A independently is N, CH or $CR^{13}$;
B is NH, O, S or $NR^{13}$;
p is 1 or 2; and
—X— is a bivalent radical selected from —$NR^{14}$—; —NH—NH—; —N=N—; —O—; —$C_{1-6}$alkanediyl— which may optionally be substituted with halo, $C_{1-6}$alkyloxy, $C_{1-6}$alkyloxycarbonyl, $C_{1-6}$alkylcarbonyloxy, mono- or di($C_{1-6}$alkyl)amino, mono- or di($C_{1-6}$alkyl)aminocarbonyl; —C(=O)—; —CHOH—; —S—; —S(=O)$_m$—; each m independently is 1 or 2;
$R^5$ and $R^6$ each independently represent hydrogen or $C_{1-4}$alkyl optionally substituted with cyano, $C_{1-4}$alkyloxy, $C_{1-4}$alkylthio, amino, mono- or di($C_{1-4}$alkyl)amino or a radical of formula

(c)

with $A_3$ and $A_4$ each independently representing $CH_2$, $NR^{12}$ or O;
$R^7$ is hydrogen, hydroxy, $C_{1-4}$alkyloxy, carboxy$C_{1-4}$alkyloxy, $C_{1-4}$alkyloxycarbonyl-$C_{1-4}$alkyloxy, $C_{2-4}$alkenyloxy, $C_{2-4}$alkynyloxy or aryl$C_{1-4}$alkyloxy;
$R^8$ is hydrogen, carboxyl or $C_{1-4}$alkyl;
$R^9$ is hydrogen; $C_{1-4}$alkyl optionally substituted with cyano, $C_{1-4}$alkyloxy, $C_{1-4}$alkyl-S(=O)$_m$—, aryl or Het$^2$; $C_{1-4}$alkyloxy; $C_{2-4}$alkenyl; aryl$C_{2-4}$alkenyl; Het$^2C_{2-4}$alkenyl; $C_{2-4}$alkynyl; Het$^2C_{2-4}$alkynyl; aryl$C_{2-4}$alkynyl; $C_{3-7}$cycloalkyl; aryl; naphthyl; or Het$^2$;
$R^{10}$ is $C_{1-4}$alkyl, aryl$C_{1-4}$alkyl, aryl, arylcarbonyl, $C_{1-4}$alkylcarbonyl, $C_{1-4}$alkyloxycarbonyl, or $C_{1-4}$alkyloxycarbonyl$C_{1-4}$alkyl;
$R^{11}$ is $C_{1-4}$alkyl optionally substituted with aryl or Het$^3$, polyhalo$C_{1-4}$alkyl, or $C_{2-4}$alkenyl optionally substituted with aryl or Het$^3$;
$R^{12}$ is hydrogen, $C_{1-4}$alkyl or $C_{1-4}$alkylcarbonyl;
$R^{13}$ is $C_{1-6}$alkyl, amino, mono- or di($C_{1-6}$alkyl)amino or polyhalo$C_{1-6}$alkyl;
$R^{14}$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; or $C_{1-6}$alkyloxy$C_{1-6}$alkylcarbonyl substituted with $C_{1-6}$alkyloxycarbonyl;
aryl is phenyl optionally substituted with one, two, three, four or five substituents each independently selected from hydroxy, halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;
Het$^1$ represents a monocyclic or bicyclic heterocycle selected from pyrrolyl, furanyl, thienyl, imidazolyl, oxazolyl, thiazolyl, pyridyl, pyrimidinyl, pyrazinyl, pyridazinyl, pyrrolidinyl, tetrahydrofuranyl, tetrahydrothienyl, imidazolidinyl, oxazolidinyl, thiazolidinyl, piperidinyl, hexahydropyrimidinyl, piperazinyl, hexahydropyridazinyl, benzofuranyl, benzothienyl, benzimidazolyl, benzoxazolyl, benzothiazolyl, quinolinyl, 2-oxo-1,2-dihydroquinolinyl, each of said monocyclic or bicyclic heterocycle may optionally be substituted with one, two or three substituents each independently selected from halo, hydroxy, $C_{1-4}$alkyl, $C_{1-4}$alkyloxy, $C_{1-4}$alkylcarbonyl or polyhalo$C_{1-4}$alkyl;
Het$^2$ represents a monocyclic or bicyclic heterocycle selected from pyrrolyl, furanyl, thienyl, imidazolyl, oxazolyl, thiazolyl, pyrazolyl, isoxazolyl, isothiazolyl, pyridinyl, pyrimidinyl, pyrazinyl, pyridazinyl, benzopyrrolyl, benzofuranyl, benzothienyl, benzimidazolyl, benzoxazolyl, benzothiazolyl, benzotriazolyl, quinolinyl, 2-oxo-1,2-dihydro-quinolinyl, quinolinonyl, pyrrolidinyl, tetrahydrofuranyl, tetrahydrothienyl, imidazolidinyl, oxazolidinyl, thiazolidinyl, piperidinyl, hexahydropyrimidinyl, piperazinyl, and hexahydropyridazinyl or a radical of formula

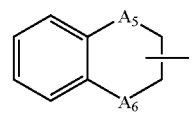
(d)

with $A_5$ or $A_6$ each independently being selected from $CH_2$ or O;
each of said monocyclic or bicyclic heterocycle may optionally be substituted with one, two or three substituents each independently selected from halo, hydroxy,$C_{1-4}$alkyl, $C_{1-4}$alkyloxy, $C_{1-4}$alkylcarbonyl, polyhalo$C_{1-4}$alkyl or aryl;
Het$^3$ represents a monocyclic heterocycle selected from pyrrolyl, furanyl, thienyl, imidazolyl, oxazolyl, thiazolyl, pyridyl, pyrimidinyl, pyrazinyl, pyridazinyl, each of said heterocycle may optionally be substituted with one, two or three substituents each independently selected from halo, hydroxy, $C_{1-4}$alkyl, $C_{1-4}$alkyloxy, $C_{1-4}$alkylcarbonyl or polyhalo$C_{1-4}$alkyl.

2. A compound as claimed in claim 1 wherein $R^1$ is hydrogen, $C_{1-6}$alkyl or aryl$C_{1-6}$alkyl; $R^2$ is hydrogen, $C_{1-6}$alkyl or arylthio; $R^3$ and $R^4$ are aryl and X is O, S or S(=O)$_m$.

3. A compound as claimed in claim 1 or 2 wherein $R^1$ is $C_{1-3}$alkyl or aryl$C_{1-6}$alkyl.

4. A compound as claimed in claim 3, wherein $R^1$ is methyl.

5. A compound as claimed in claim 1, wherein $R^2$ is methyl.

6. A compound as claimed in claim 1, wherein $R^3$ or $R^4$ is phenyl substituted with one, two or three substituents selected from cyano, aminocarbonyl, $C_{1-6}$alkyl, halo, polyhalo$C_{1-6}$alkyl.

7. A compound as claimed in claim 1, wherein $R^4$ is phenyl substituted with one of cyano, aminocarbonyl, $C_{1-6}$alkyl, halo, and polyhalomethyl.

8. A compound as claimed in claim 1 wherein the compound is one of:
4-[[3,4-dihydro-4-methyl-6-(2-methylphenoxy)-3-oxopyrazinyl]amino]-benzonitrile;
4-[[6-(2,4-dimethylphenoxy)-3,4-dihydro-4-methyl-3-oxopyrazinyl]amino]-benzonitrile;
4-[[3,4-dihydro-4-methyl-6-[(2-methylphenyl)thio]-3-oxopyrazinyl]amino]-benzonitrile;
3-[(4-chlorophenyl)amino]-1,6-dimethyl-5-(2-methylphenoxy)-2(1H)-pyrazinone;
5-(2,4-dimethylphenoxy)-1-methyl-3-(phenylamino)-2 (1H)-pyrazinone;

3-[(4-chlorophenyl)amino]-5-[(2,4-dimethylphenyl)
thio]-1,6-dimethyl-2(1H)-pyrazinone;
4-[[6-(2,4-dimethylphenoxy)-3,4-dihydro-3-oxo-4-(phenylmethyl)pyrazinyl]amino]-benzonitrile;
4-[[6-(2,4-dimethylphenoxy)-3,4-dihydro-3-oxo-4-(phenylmethyl)pyrazinyl]amino]-benzonitrile;
5-(2,4-dimethylphenoxy)-1-methyl-3-[[4-(trifluoromethyl)phenyl]amino]-2(1H)-pyrazinone;
5-(2,4-dimethylphenoxy)-1-methyl-3-[[4-(trifluoromethyl)phenyl]amino]-2(1H)-pyrazinone;
4-[[3,4-dihydro-4-methyl-3-oxo-6-[(2,4,6-trimethylphenyl)thio]pyrazinyl]amino]-benzonitrile;
3-[(4-chlorophenyl)amino]-1-methyl-5-[(2,4,6-trimethylphenyl)thio]-2(1H)-pyrazinone;
4-[[3,4-dihydro-4-methyl-3-oxo-6-[(2,4,6-trimethylphenyl)sulfonyl]pyrazinyl]amino]-benzonitrile;
4-[[6-[(2,4-dimethylphenyl)sulfonyl]-3,4-dihydro-4,5-dimethyl-3-oxopyrazinyl]amino]-benzonitrile;
4-[[3,4-dihydro-4,5-dimethyl-3-oxo-6-[(2,4,6-trimethylphenyl)sulfonyl]pyrazinyl]amino]-benzonitrile;
4-[[3,4-dihydro-4,5-dimethyl-3-oxo-6-[(2,4,6-trimethylphenyl)sulfonyl]pyrazinyl]amino]-benzonitrile;
4-[[3,4-dihydro-4,5-dimethyl-6-(2-methylphenoxy)-3-oxopyrazinyl]amino]-benzonitrile;
4-[[6-(2,4-dimethylphenoxy)-3,4-dihydro-4,5-dimethyl-3-oxopyrazinyl]amino]-benzonitrile;
4-[[6-[(2,4-dimethylphenyl)thio]-3,4-dihydro-4-methyl-3-oxopyrazinyl]amino]-benzonitrile;
3-[(4-chlorophenyl)amino]-5-(2,4-dimethylphenoxy)-1-methyl-2(1H)-pyrazinone;
3-[(4-chlorophenyl)amino]-5-(2,4-dimethylphenoxy)-1,6-dimethyl-2(1H)-pyrazinone;
4-[[3,4-dihydro-4,5-dimethyl-6-[(2-methylphenyl)thio]-3-oxopyrazinyl]amino]-benzonitrile;
3-[(4-chlorophenyl)amino]-5-(2,4-dimethylphenylthio)-1,6-dimethyl-2(1H)-pyrazinone;
4-[[6-[(4-cyanophenyl)amino]-4,5-dihydro-3,4-dimethyl-5-oxopyrazinyl]oxy]-3,5-dimethyl-benzonitrile;
4-[4,5-dimethyl-3-oxo-6-(2,4,6-trimethyl-phenylsulfanyl)-3,4-dihydro-pyrazin-2-ylamino]-benzonitrile;
4-[[6-[(2-methylphenyl)thio]-5-methyl-3,4-dihydro-3-oxo-4-(phenylmethyl)pyrazinyl]amino]-benzonitrile;
4-[[3,4-dihydro-5-methyl-6-[(2-methylphenyl)thio]-3-oxopyrazinyl]amino]-benzonitrile;
4-[[6-(2,4-dimethylphenoxy)-5-methyl-3,4-dihydro-3-oxo-4-(phenylmethyl)pyrazinyl]amino]-benzonitrile;
5-(2,4,6-trimethylphenoxy)-5-methyl-1-methyl-3-[[4-(trifluoromethyl)phenyl]amino]-2(1H)-pyrazinone;
a N-oxide, a pharmaceutically acceptable addition salt, a quaternary amine and a stereochemically isomeric form thereof.

9. A compound as claimed in claim 8 wherein the compound is one of:
4-[[3,4-dihydro-4-methyl-6-(2-methylphenoxy)-3-oxopyrazinyl]amino]-benzonitrile;
4-[[6-(2,4-dimethylphenoxy)-3,4-dihydro-4-methyl-3-oxopyrazinyl]amino]-benzonitrile;
4-[[3,4-dihydro-4-methyl-6-[(2-methylphenyl)thio]-3-oxopyrazinyl]amino]-benzonitrile;
3-[(4-chlorophenyl)amino]-1,6-dimethyl-5-(2-methylphenoxy)-2(1H)-pyrazinone;
5-(2,4-dimethylphenoxy)-1-methyl-3-(phenylamino)-2(1H)-pyrazinone;
3-[(4-chlorophenyl)amino]-5-[(2,4-dimethylphenyl)thio]-1,6-dimethyl-2(1H)-pyrazinone;
4-[[6-(2,4-dimethylphenoxy)-3,4-dihydro-3-oxo-4-(phenylmethyl)pyrazinyl]amino]-benzonitrile,
4-[[6-(2,4-dimethylphenoxy)-3,4-dihydro-3-oxo-4-(phenylmethyl)pyrazinyl]amino]-benzonitrile;
5-(2,4-dimethylphenoxy)-1-methyl-3-[[4-(trifluoromethyl)phenyl]amino]-2(1H)-pyrazinone;
5-(2,4-dimethylphenoxy)-1-methyl-3-[[4-(trifluoromethyl)phenyl]amino]-2(1H)-pyrazinone;
4-[[3,4-dihydro-4-methyl-3-oxo-6-[(2,4,6-trimethylphenyl)thio]pyrazinyl]amino]-benzonitrile;
3-[(4-chlorophenyl)amino]-1-methyl-5-[(2,4,6-trimethylphenyl)thio]-2(1H)-pyrazinone,
4-[[3,4-dihydro-4-methyl-3-oxo-6-[(2,4,6-trimethylphenyl)sulfonyl]pyrazinyl]amino]-benzonitrile;
4-[[6-[(2,4-dimethylphenyl)sulfonyl]-3,4-dihydro-4,5-dimethyl-3-oxopyrazinyl]amino]-benzonitrile,
4-[[3,4-dihydro-4,5-dimethyl-3-oxo-6-[(2,4,6-trimethylphenyl)sulfonyl]pyrazinyl]amino]-benzonitrile;
4-[[3,4-dihydro-4,5-dimethyl-3-oxo-6-[(2,4,6-trimethylphenyl)sulfinyl]pyrazinyl]amino]-benzonitrile;
4-[[3,4-dihydro-4,5-dimethyl-6-(2-methylphenoxy)-3-oxopyrazinyl]amino]benzonitrile,
4-[[6-(2,4-dimethylphenoxy)-3,4-dihydro-4,5-dimethyl-3-oxopyrazinyl]amino]-benzonitrile
4-[[6-[(2,4-dimethylphenyl)thio]-3,4-dihydro-4-methyl-3-oxopyrazinyl]amino]-benzonitrile;
3-[(4-chlorophenyl)amino]-5-(2,4-dimethylphenoxy)-1-methyl-2(1H)-pyrazinone;
3-[(4-chlorophenyl)amino]-5-(2,4-dimethylphenoxy)-1,6-dimethyl-2(1H)-pyrazinone;
4-[[3,4-dihydro-4,5-dimethyl-6-[(2-methylphenyl)thio]-3-oxopyrazinyl]amino]-benzonitrile;
3-[(4-chlorophenyl)amino]-5-(2,4-dimethylphenylthio)-1,6-dimethyl-2(1H)-pyrazinone;
4-[[6-[(4-cyanophenyl)amino]-4,5-dihydro-3,4-dimethyl-5-oxopyrazinyl]oxy]-3,5-dimethyl-benzonitrile;
4-[4,5-dimethyl-3-oxo-6-(2,4,6-trimethyl-phenylsulfanyl)-3,4-dihydro-pyrazin-2-ylamino]-benzonitrile;
a N-oxide, a pharmaceutically acceptable addition salt, a quaternary amine and a stereochemically isomeric form thereof.

10. A compound as claimed in claim 8, wherein the compound is one of:
4-[[3,4-dihydro-4,5-dimethyl-6-(2-methylphenoxy)-3-oxopyrazinyl]amino]-benzonitrile;
4-[[6-(2,4-dimethylphenoxy)-3,4-dihydro-4,5-dimethyl-3-oxopyrazinyl]amino]-benzonitrile;
4-[[6-[(2,4-dimethylphenyl)thio]-3,4-dihydro-4-methyl-3-oxopyrazinyl]amino]-benzonitrile;
4-[[6-[(4-cyanophenyl)amino]-4,5-dihydro-3,4-dimethyl-5-oxopyrazinyl]oxy]-3,5-dimethyl-benzonitrile; a N-oxide, a pharmaceutically acceptable addition salt, a quaternary amine and a stereochemically isomeric form thereof.

11. A method for the treatment of HIV (Human Immunodeficiency Virus) infection, comprising administering to a subject in need thereof a medicament that comprises a therapeutically effective amount of a compound as claimed in any one of claims 1–10.

12. A method for the treatment of multi drug resistant HIV infection, comprising administering to a subject in need thereof a therapeutically effective amount of a compound as claimed in claim 1.

13. A pharmaceutical composition comprising a pharmaceutically acceptable carrier and as active ingredient a compound as claimed in claim 1.

14. A process for preparing a pharmaceutical composition, comprising intimately mixing a compound as claimed in claim 1 with a pharmaceutically acceptable carrier.

15. A product comprising (a) a compound as claimed in claim 1, and (b) another antiretroviral compound.

16. A pharmaceutical composition comprising a pharmaceutically acceptable carrier and as active ingredients (a) a compound as claimed in any one of claims 1 to 10, and (b) another antiretroviral compound.

17. A method for treating an HIV infection, comprising administering to a subject in need thereof a therapeutically effective amount of a product according to claim is, wherein said constituents (a) and (b) are administered simultaneously separately, or sequentially.

18. A process for preparing a compound as claimed in claim 1, comprising reacting an intermediate of formula (II), wherein $W_1$ represents a suitable leaving group, with an intermediate of formula (III) in the presence of a suitable catalyst, a suitable base, and a suitable solvent,

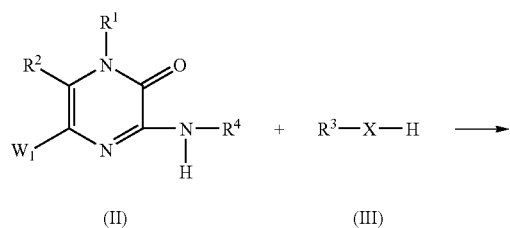

-continued

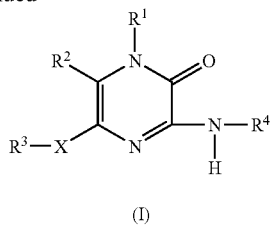

with $R^1$, $R^2$, $R^3$, $R^4$ and X as defined in claim 1.

19. A process according to claim 18, wherein said reacting is performed at a temperature of about 110° C. or greater.

20. A process according to claim 18, further comprising converting compounds of formula (I) into each other.

21. A process according to claim 18, further comprising converting compounds of formula (I), into a therapeutically active non-toxic acid addition salt by treatment with an acid.

22. A process according to claim 21, further comprising converting the acid addition salt into a free base by treatment with alkali.

23. A process according to claim 18, further comprising preparing a stereochemically isomeric form of said compound or a N-oxide form of said compound.

* * * * *